(12) United States Patent
Silbart et al.

(10) Patent No.: US 11,745,001 B2
(45) Date of Patent: Sep. 5, 2023

(54) THERAPEUTIC BANDAGE

(71) Applicant: University of Connecticut, Farmington, CT (US)

(72) Inventors: Lawrence Silbart, Farmington, CT (US); Thanh Duc Nguyen, South Windsor, CT (US)

(73) Assignee: University of Connecticut, Farmington, CT (US)

(*) Notice: Subject to any disclaimer, the term of this patent is extended or adjusted under 35 U.S.C. 154(b) by 346 days.

(21) Appl. No.: 17/197,624

(22) Filed: Mar. 10, 2021

(65) Prior Publication Data
US 2021/0283387 A1    Sep. 16, 2021

Related U.S. Application Data

(60) Provisional application No. 62/987,494, filed on Mar. 10, 2020.

(51) Int. Cl.
*A61M 37/00* (2006.01)
*A61L 15/22* (2006.01)
*A61L 15/44* (2006.01)

(52) U.S. Cl.
CPC ....... *A61M 37/0015* (2013.01); *A61L 15/225* (2013.01); *A61L 15/44* (2013.01);
(Continued)

(58) Field of Classification Search
CPC ...... A61M 37/0015; A61M 2037/0023; A61M 2037/0061; A61L 15/225; A61L 15/44;
(Continued)

(56) References Cited

U.S. PATENT DOCUMENTS 4,438,773 A    3/1984    Letterio
5,131,276 A    7/1992    Kibblewhite
(Continued)

FOREIGN PATENT DOCUMENTS

CN    102657914 B    5/2015
CN    106109792 A    11/2016
(Continued)

OTHER PUBLICATIONS

Curry et al., Supporting Information Appendix Biodegradable piezoelectric force sensor PNAS. Jan. 2018 pp. 1-33 (Year: 2018).
(Continued)

*Primary Examiner* — Amber R Stiles
(74) *Attorney, Agent, or Firm* — Michael Best & Friedrich LLP

(57) ABSTRACT

A therapeutic bandage includes a bandage matrix and an array of microneedles extending from the bandage matrix. Each of the microneedles includes a first layer that encapsulates a first immunomodulatory compound and a second layer that encapsulates a second immunomodulatory compound. The array of microneedles is configured to guide foreign agents affected by the first immunomodulatory compound, the second immunomodulatory compound, or the first and second immunomodulatory compounds from one or more skin layers of a user to the bandage matrix such that the bandage matrix absorbs and captures the foreign agents.

20 Claims, 8 Drawing Sheets
(1 of 8 Drawing Sheet(s) Filed in Color)

(52) U.S. Cl.
CPC .............. *A61M 2037/0023* (2013.01); *A61M 2037/0061* (2013.01)

(58) Field of Classification Search
CPC ......... A61L 2300/256; A61L 2300/404; A61L 2300/442; A61L 2300/62; A61L 15/26
See application file for complete search history.

(56) References Cited

U.S. PATENT DOCUMENTS

| | | |
|---|---|---|
| 5,246,013 A | 9/1993 | Frank et al. |
| 5,287,331 A | 2/1994 | Schindel et al. |
| 5,306,620 A | 4/1994 | Ginsberg et al. |
| 5,443,495 A | 8/1995 | Buscemi et al. |
| 5,498,499 A | 3/1996 | Flow et al. |
| 5,512,600 A | 4/1996 | Mikos et al. |
| 5,514,378 A | 5/1996 | Mikos et al. |
| 5,678,565 A | 10/1997 | Sarvazyan |
| 5,697,901 A | 12/1997 | Eriksson |
| 5,794,023 A | 8/1998 | Hobbs et al. |
| 5,827,198 A | 10/1998 | Kassal |
| 5,891,191 A | 4/1999 | Stinson |
| 6,142,948 A | 11/2000 | Toda |
| 6,219,574 B1 | 4/2001 | Cormier et al. |
| 6,334,856 B1 | 1/2002 | Allen et al. |
| 6,447,887 B1 | 9/2002 | Claus et al. |
| 6,468,219 B1 | 10/2002 | Njemanze |
| 6,627,421 B1 | 9/2003 | Unger et al. |
| 6,835,377 B2 | 12/2004 | Goldberg et al. |
| 7,001,372 B2 | 2/2006 | Richter |
| 7,184,826 B2 | 2/2007 | Cormier et al. |
| 7,332,197 B2 | 2/2008 | Wood et al. |
| 7,344,499 B1 | 3/2008 | Prausnitz et al. |
| 7,396,537 B1 | 7/2008 | Krupnick et al. |
| 7,879,093 B2 | 2/2011 | Wei et al. |
| 7,906,223 B2 | 3/2011 | Rakow et al. |
| 8,067,110 B2 | 11/2011 | Rakow et al. |
| 8,162,901 B2 | 4/2012 | Gonnelli et al. |
| D659,820 S | 5/2012 | Abel et al. |
| 8,301,262 B2 | 10/2012 | Mi et al. |
| 8,469,936 B2 | 6/2013 | Robinson et al. |
| 8,708,966 B2 | 4/2014 | Allen et al. |
| 8,798,932 B2 | 8/2014 | Boyden et al. |
| 8,946,974 B2 | 2/2015 | Yu et al. |
| 8,955,515 B2 | 2/2015 | Rakow et al. |
| 9,040,087 B2 | 5/2015 | Boyden et al. |
| 9,050,053 B2 | 6/2015 | Morgan |
| 9,089,677 B2 | 7/2015 | Soo et al. |
| 9,192,655 B2 | 11/2015 | Arinzeh et al. |
| 9,381,680 B2 | 7/2016 | Oh et al. |
| 9,444,030 B2 | 9/2016 | Wang et al. |
| 9,527,257 B2 | 12/2016 | Lipton et al. |
| 9,795,774 B2 | 10/2017 | Takada et al. |
| 9,846,091 B2 | 12/2017 | Lu et al. |
| 9,849,270 B2 | 12/2017 | Stockholm |
| 10,004,790 B2 | 6/2018 | D'Souza |
| 10,098,574 B1 | 10/2018 | Kam |
| 10,245,421 B2 | 4/2019 | Ross |
| 10,292,831 B2 | 5/2019 | Zellmer et al. |
| 10,500,300 B2 | 12/2019 | Dybe et al. |
| 10,617,880 B2 | 4/2020 | Zellmer et al. |
| 10,632,653 B2 | 4/2020 | Niitsu et al. |
| 10,710,011 B2 | 7/2020 | Inoue et al. |
| 2002/0081732 A1 | 6/2002 | Bowlin et al. |
| 2002/0082543 A1 | 6/2002 | Park et al. |
| 2004/0015211 A1 | 1/2004 | Nurmikko et al. |
| 2004/0018226 A1 | 1/2004 | Wnek et al. |
| 2004/0028655 A1 | 2/2004 | Nelson et al. |
| 2005/0248547 A1 | 11/2005 | Kent et al. |
| 2006/0043843 A1 | 3/2006 | Sugiura et al. |
| 2006/0050189 A1 | 3/2006 | Ito et al. |
| 2006/0107749 A1 | 5/2006 | Liu et al. |
| 2006/0190080 A1 | 8/2006 | Danoff et al. |
| 2006/0224237 A1 | 10/2006 | Furst et al. |
| 2007/0141106 A1 | 6/2007 | Bonutti et al. |
| 2007/0225631 A1 | 9/2007 | Bowlin et al. |
| 2007/0255422 A1 | 11/2007 | Wei et al. |
| 2007/0270738 A1 | 11/2007 | Wu et al. |
| 2007/0293912 A1 | 12/2007 | Cowan et al. |
| 2008/0009802 A1 | 1/2008 | Lambino et al. |
| 2008/0058633 A1 | 3/2008 | Boyden et al. |
| 2008/0269666 A1 | 10/2008 | Wang et al. |
| 2009/0030365 A1 | 1/2009 | Tokumoto et al. |
| 2009/0062723 A1 | 3/2009 | Skiba |
| 2009/0163965 A1 | 6/2009 | Boyden et al. |
| 2009/0182306 A1 | 7/2009 | Lee et al. |
| 2009/0192431 A1 | 7/2009 | Horstmann et al. |
| 2009/0280153 A1 | 11/2009 | Hunter et al. |
| 2010/0152644 A1 | 6/2010 | Pesach et al. |
| 2011/0028905 A1 | 2/2011 | Takada |
| 2011/0109204 A1 | 5/2011 | Tajitsu et al. |
| 2011/0230747 A1 | 9/2011 | Rogers et al. |
| 2011/0242310 A1 | 10/2011 | Beebe et al. |
| 2012/0197155 A1 | 8/2012 | Mattes et al. |
| 2012/0226295 A1 | 9/2012 | Jabbari |
| 2013/0005708 A1 | 1/2013 | Lalwani |
| 2013/0041244 A1 | 2/2013 | Woias et al. |
| 2013/0086703 A1 | 4/2013 | Maruyama et al. |
| 2013/0140649 A1 | 6/2013 | Rogers et al. |
| 2014/0005606 A1 | 1/2014 | Chen et al. |
| 2014/0145365 A1 | 5/2014 | Omenetto et al. |
| 2014/0170299 A1 | 6/2014 | Gill et al. |
| 2014/0316353 A1 | 10/2014 | Riesinger |
| 2014/0333184 A1 | 11/2014 | Wang et al. |
| 2015/0073551 A1 | 3/2015 | Uehlin |
| 2015/0134061 A1 | 5/2015 | Friis et al. |
| 2015/0165020 A1 | 6/2015 | Jaklenec et al. |
| 2016/0005951 A1 | 1/2016 | Yoshida et al. |
| 2016/0050750 A1 | 2/2016 | Rogers et al. |
| 2016/0067375 A1 | 3/2016 | Holmes et al. |
| 2016/0095599 A1 | 4/2016 | Jose et al. |
| 2016/0175408 A1 | 6/2016 | Chang et al. |
| 2016/0184571 A1 | 6/2016 | Admati |
| 2016/0184595 A1 | 6/2016 | Hossainy |
| 2016/0190427 A1 | 6/2016 | Kim et al. |
| 2016/0287668 A1 | 10/2016 | Tankovich |
| 2017/0020402 A1 | 1/2017 | Rogers et al. |
| 2017/0027168 A1 | 2/2017 | Heath |
| 2017/0080196 A1 | 3/2017 | Lee et al. |
| 2017/0179370 A1 | 6/2017 | Kim et al. |
| 2017/0189660 A1 | 7/2017 | Baek |
| 2017/0252546 A1 | 9/2017 | Park et al. |
| 2017/0258738 A1 | 9/2017 | DeMuth et al. |
| 2017/0268942 A1 | 9/2017 | Pedder et al. |
| 2017/0306295 A1 | 10/2017 | Hazot et al. |
| 2017/0348218 A1 | 12/2017 | Chen et al. |
| 2017/0368321 A1 | 12/2017 | Baek |
| 2018/0055643 A1 | 3/2018 | Castro et al. |
| 2018/0140817 A1 | 5/2018 | Spector |
| 2018/0256905 A1 | 9/2018 | Francia et al. |
| 2018/0289616 A1 | 10/2018 | Chen et al. |
| 2018/0325806 A1 | 11/2018 | Litvack et al. |
| 2019/0142318 A1 | 5/2019 | Diebold et al. |
| 2019/0209819 A1 | 7/2019 | Ross |
| 2019/0217071 A1 | 7/2019 | Engel et al. |
| 2019/0269895 A1 | 9/2019 | Nguyen et al. |
| 2019/0307697 A1 | 10/2019 | Ma et al. |
| 2019/0319181 A1 | 10/2019 | Melandso et al. |
| 2019/0328285 A1 | 10/2019 | Liu |
| 2019/0330771 A1 | 10/2019 | Takumi et al. |
| 2020/0009767 A1 | 1/2020 | Li |
| 2020/0093966 A1 | 3/2020 | Rabolt et al. |
| 2020/0276018 A1 | 9/2020 | Nguyen et al. |
| 2020/0276365 A1 | 9/2020 | Nguyen et al. |
| 2020/0282350 A1 | 9/2020 | Inoue et al. |
| 2020/0292206 A1 | 9/2020 | Tamakura et al. |
| 2020/0313066 A1 | 10/2020 | Getman |
| 2021/0127998 A1 | 5/2021 | Nguyen et al. |
| 2021/0378949 A1 | 12/2021 | Nguyen et al. |
| 2021/0379249 A1 | 12/2021 | Nguyen et al. |
| 2022/0096371 A1 | 3/2022 | Nguyen et al. |

(56) References Cited

U.S. PATENT DOCUMENTS

| | | | |
|---|---|---|---|
| 2022/0176171 | A1 | 6/2022 | Nguyen et al. |
| 2023/0073125 | A1* | 3/2023 | Hasani-Sadrabadi ........................ A61K 47/34 |

FOREIGN PATENT DOCUMENTS

| | | |
|---|---|---|
| EP | 0955359 B1 | 1/2009 |
| EP | 1993621 B1 | 8/2011 |
| EP | 1715915 B1 | 11/2012 |
| EP | 2482772 B1 | 10/2018 |
| EP | 3542740 A1 | 9/2019 |
| IN | 202041031484 A | 7/2020 |
| KR | 101832716 B1 | 2/2018 |
| RU | 2082467 C1 | 6/1997 |
| WO | WO 2006057987 A1 | 6/2006 |
| WO | WO 2008085904 A1 | 7/2008 |
| WO | WO 2012103257 A2 | 8/2012 |
| WO | WO 2012127224 A1 | 9/2012 |
| WO | 2013101908 A1 | 7/2013 |
| WO | WO 2014143412 A8 | 11/2014 |
| WO | WO 2017003238 A1 | 1/2017 |
| WO | WO 2017011320 A1 | 1/2017 |
| WO | WO 2017139253 A1 | 8/2017 |
| WO | WO 2017151715 A1 | 9/2017 |
| WO | 2017191542 A1 | 11/2017 |
| WO | 2018017196 A1 | 1/2018 |
| WO | 2018089918 A1 | 5/2018 |
| WO | 2018114871 A1 | 6/2018 |
| WO | WO 2018170132 A1 | 9/2018 |
| WO | 2019025625 A1 | 2/2019 |
| WO | 2019094349 A1 | 5/2019 |
| WO | WO 2019143293 A1 | 7/2019 |

OTHER PUBLICATIONS

International Search Report and Written Opinion for Application No. PCT/US2021/021677 dated Jun. 22, 2021 (15 pages).
Bagherbaigi et al., "Cotton fabric as an immobilization matrix for low-cost and quick colorimetric enzyme-linked immunosorbent assay (ELISA)," Analytical Methods, (2014), 6:7175-7180.
ABCAM. ELISA kit for MCP-1. https://www.abcam.com/rat-mcp1-ehsa-kit-ab219045.html. Accessed Aug. 22, 2022 (5 pages).
ABCAM. ELISA kit for TNF-alpha. https://www.abcam.com/rat-tnf-alpha-elisa-kit-ab236712.html. Accessed Aug. 22, 2022 (5 pages).
AFPRO Filters. Pm1: The Most Hazardous Kind of Particulate Matter. https://web.archive.org/web/20200609213853/https://www.afprofilters.com/pm1-airfilter/, Jun. 9, 2020, (4 pages).
Ager, D. J. et al. Stability of aspirin in solid mixtures. Journal of pharmaceutical sciences 1986, 75, (1), 97-101.
Alemdaroğlu, C.; et al. An investigation on burn wound healing in rats with chitosan gel formulation containing epidermal growth factor. Burns 2006, 32, (3), 319-327.
Alneami AQ, et al. Effect of Electrical Current Stimulation on Pseudomonas Aeruginosa Growth. Journal of Physics: Conference Series. 2018;1003:012112.
Amini et al., "Bone tissue engineering: recent advances and challenges," Critical Reviews™ in Biomedical Engineering, 2012, 40,(5):363-408.
Amirnasr, E. et al. Basis Weight Uniformity Analysis in Nonwovens. The Journal of the Textile Institute 2014, 105 (4), 444-453.
Ando et al., "Film sensor device fabricated by a piezoelectric poly(L-lactic acid) film", 2012, Jpn J Appl Phys 51:09LD14.
Ando et al., "Pressure-sensitive touch panel based on piezoelectric poly (l-lactic acid) film", 2013, Jpn. J. Appl. Phys. 52:09KD17.
Ando et al., "New human machine interface devices using a piezoelectric poly(L-lactic acid) film" in 2013 IEEE International Symposium on the Applications of Ferroelectric and Workshop on the Piezoresponse Force Microscopy (ISAF/PFM) (IEEE, 2013), pp. 236-239.
Anglen, "The clinical use of bone stimulators," Journal of the Southern Orthopaedic Association, 2002, 12, (2), 46-54.
Arakha M, et al. The effects of interfacial potential on antimicrobial propensity of ZnO nanoparticle. Scientific Reports. 2015;5(1):9578.
Asadimr, et al. Bacterial Inhibition by Electrical Stimulation. Advances in Wound Care. 2013;3(2):91-97.
Atkins et al. Raman spectroscopy of blood and blood components. Appl. Spectrosc. 71, 767-793 (2017).
Babu, R. et al. Assessment of skin irritation and molecular responses in rat skin exposed to nonane, dodecane and tetradecane. Toxicology letters 2004, 153, (2), 255-266.
Bai, Y.; et al. Washable Multilayer Triboelectric Air Filter for Efficient Particulate Matter Pm2. 5 Removal. Advanced Functional Materials 2018, 28 (15), 1706680.
Baker, B., et al. Electrical stimulation of articular cartilage regeneration. Annals of the New York Academy of Sciences 238, 491-499 (1974).
Banerjee J, et al. Silver-zinc redox-coupled electroceutical wound dressing disrupts bacterial biofilm. PLoS One. 2015; 10(3):e0119531-e0119531.
Barbour, K. E.; et al., Prevalence of doctor-diagnosed arthritis and arthritis-attributable activity limitation—United States, 2010-2012. MMWR. Morbidity and mortality weekly report 2013, 62, (44), 869-873.
Barbour, K. E.; et al., Vital signs: prevalence of doctor-diagnosed arthritis and arthritis-attributable activity limitation—United States, 2013-2015. MMWR. Morbidity and mortality weekly report 2017, 66, (9), 246-253.
Barki KG, et al. Electric Field Based Dressing Disrupts Mixed-Species Bacterial Biofilm Infection and Restores Functional Wound Healing. Ann Surg. 2019;269(4).
Barton, N. J.; et al., Demonstration of a novel technique to quantitatively assess inflammatory mediators and cells in rat knee joints. Journal of Inflammation 2007, 4, (1), 13.
Bastaki, S. M.; et al. Effect of Aspirin and ibuprofen either alone or in combination on gastric mucosa and bleeding time and on serum prostaglandin E 2 and thromboxane A 2 levels in the anaesthetized rats in vivo. Molecular and cellular biochemistry 2018, 438, (1-2), 25-34.
Bauer et al., "Bone Graft Materials: An Overview of the Basic Science," Clinical orthopaedics and related research, 2000, 371, 10-27.
Bello et al., "Development of a smart pump for monitoring and controlling intraocular pressure", Ann Biomed Eng 45:990-1002, 2017.
Bergsma JE, et al. Late degradation tissue response to poly(l-lactide) bone plates and screws. Biomaterials. 1995;16(1):25-31.
Besinis, A.; et al. Antibacterial activity and biofilm inhibition by surface modified titanium alloy medical implants following application of silver, titanium dioxide and hydroxyapatite nanocoatings. Nanotoxicology 2017, 11, (3), 327-338.
Bir SC, et al. Control of angiogenesis dictated by picomolar superoxide levels. Free Radic Biol Med. 2013;63:135-142.
Bloomberg News. Mask Mandates by Nation Most Still Await a Breath of Fresh Air. https://www.bloomberg.com/news/articles/2021-05-14/mask-mandates-by-nation-most-still-await-a-breath-of-fresh-air. May 14, 2021 (9 pages).
Boks NP, et al. Forces involved in bacterial adhesion to hydrophilic and hydrophobic surfaces. Microbiology. 2008;154(Pt 10):3122-3133.
Bos et al., "Resorbable poly(L-lactide) plates and screws for the fixation of zygomatic fractures", 1987, J Oral Maxillofac Surg, 45:751-753.
Bose, S.; et al. A review on advances of sustained release drug delivery system, Int. Res. J. Pharm 2013, 4, 1-4.
Boster Bio. ELISA kit for IL-1 alpha. https://www.bosterbio.com/rat-il-1-alpha-picokine-trade-elisa-kit-ek0390-boster.html#bs_references. Jul. 1, 2013. Accessed on Aug. 22, 2022. (8 pages).
Bottino, M. C. et al. in Biomaterials for Oral and Craniomaxillofacial Applications vol. 17 90-100 (Karger Publishers, 2015).
Boutry et al., "A sensitive and Biodegradable Pressure Sensor Array for Cardiovascular Monitoring", Advanced Materials, 27, 2015, pp. 6954-6961.

(56) References Cited

OTHER PUBLICATIONS

Boutry et al., A stretchable and biodegradable strain and pressure sensor for orthopaedic application. Nat. Electron. 1, 314-321 (2018).
Boutry et al., Biodegradable and flexible arterial-pulse sensor for the wireless monitoring of blood flow. Nat. Biomed. Eng. 3, 47-57 (2019).
Bronaugh, R. L.; et al., Differences in permeability of rat skin related to sex and body site. J. Soc. Cosmet. Chem 1983, 34, (12), 127-135.
Brooks, J. T.; et al., Effectiveness of Mask Wearing to Control Community Spread of Sars-Cov-2. Jama 2021, 325 (10), 998-999.
Brune, K.; et al. Recent Insight into the Mechanism of Gastrointestinal Tract Ulceration. Scandinavian Journal of Rheumatology 1987, 16, (sup65), 135-140.
Bussemer et al., "Pulsatile drug-delivery systems," Crit Rev Ther Drug Syst., 2001, 18(5):433-458, Abstract.
Byrne, J. D.; et al., Injection Molded Autoclavable, Scalable, Conformable (Imasc) System for Aerosol-Based Protection: A Prospective Single-Arm Feasibility Study. BMJ open 2020, 10 (7), e039120.
Caballe-Serrano, J. et al. On the search of the ideal baiiier membrane for guided bone regeneration. Journal of clinical and experimental dentistry 10, e477 (2018).
Cadavid, A. P., Aspirin: the mechanism of action revisited in the context of pregnancy complications. Frontiers in immunology 2017, 8, 261.
Campbell, C. L. et al. Aspirin dose for the prevention of cardiovascular disease: a systematic review. Jama 2007, 297, (18), 2018-2024.
Carpentier et al., "Clinical trial of blood-brain barrier disruption by pulsed ultrasound," Science translational medicine, 2016, 8(343):343re2, 9 pages.
Carvalho, E. O., et al. "Tailoring bacteria response by piezoelectric stimulation." ACS applied materials & interfaces 11.30 (2019): 27297-27305.
Caspani, M. Delta Variant Pushes Us Cases Hospitalizations 6 Month High. Aug. 9, 2021. https://web.archive.org/web/20210809174911/https://www.reuters.com/world/us/delta-variant-pushes-us-cases-hospitalizations-6-month-high-2021-08-09/ (12 pages).
CDC. Antibiotic resistance threats in the United States, 2019. US Department of Health and Human Services. 2019 (150 pages).
CDC. Implementing Filtering Facepiece Respirator (Ffr) Reuse, Including Reuse after Decontamination, When There are Known Shortages of N95 Respirators, https://www.cdc.gov/coronavirus/2019-ncov/hcp/ppe-strategy/decontamination-reuse-respirators.html, Oct. 19, 2020, (10 pages).
CDC. Periodontal Disease, <https://www.cdc.gov/oralhealth/conditions/periodontal-disease.html> (Jul. 10, 2013) (3 pages).
CDC. Personal Protective Equipment: Questions and Answers, https://www.cdc.gov/coronavirus/2019-ncov/hcp/respirator-use-faq.html (Apr. 9, 2021) (6 pages).
Chang et al., Biodegradable electronic systems in 3D, heterogeneously integrated formats. Adv. Mater. 30, 1704955 (2018).
Chatterjee, A.; et al., In vitro and in vivo comparison of dermal irritancy of jet fuel exposure using EpiDerm™ (EPI-200) cultured human skin and hairless rats. Toxicology letters 2006, 167, (2), 85-94.
Chee et al., "An investigation of array of piezoelectric transducer for raindrop energy harvesting application", 2016, IEEE Region Tenth Conference, pp. 3771-3774.
Chen et al., "Fully embeddable chitosan microneedles as a sustained release depot for intradermal vaccination," Biomaterials, 2013, 34(12):3077-3086.
Chen, C.-C.; et al. Aerosol Penetration through Surgical Masks. American journal of infection control 1992, 20(4), 177-184.
Chen, M.-C. et al. Implantable polymeric microneedles with phototriggerable properties as a patient-controlled transdermal analgesia system. Journal of Materials Chemistry B 2017, 5, (3), 496-503.
Cheng, Y.; et al. Face Masks Effectively Limit the Probability of Sars-Cov-2 Transmission. Science 2021 1439-1443.
Chiappini et al., "Biodegradable silicon nanoneedles delivering nucleic acids intracellularly induce localized in vivo neovascularization," Nature Materials, 2015, 14:532-539.
Choi, S.; et al. Biodegradable, Efficient, and Breathable Multi-Use Face Mask Filter. Advanced Science 2021, 8(6), 2003155.
Chorsi MT, et al. Piezoelectric Biomaterials for Sensors and Actuators. Advanced Materials. 2019;31(1):1802084.
Chu et al., "Piezoelectric stimulation by ultrasound facilitates chondrogenesis of mesenchymal stem cells", J Acoustical Society of American, 2020, vol. 148, No. 1, pp. EL58-EL64.
Chu, D. K.; et al. Physical Distancing, Face Masks, and Eye Protection to Prevent Person-to-Person Transmission of Sars-Cov-2 and Covid-19: A Systematic Review and Meta-Analysis. The lancet 2020, 395 (10242), 1973-1987.
Chu, J.; et al. Thinking Green: Modelling Respirator Reuse Strategies to Reduce Cost and Waste. BMJ open 2021, 11(7), e048687.
Clearfield, D. S., et al. Osteochondral Differentiation of Fluorescent Multireporter Cells on Zonally-Organized Biomaterials. Tissue Engineering Part A 25, 468-486 (2019).
Cohen et al., "Totally implanted direct current stimulator as treatment for a nonunion in the foot," The Journal of foot and ankle surgery: official publication of the American College of Foot and Ankle Surgeons, 1993, 32, (4), 375-381.
Cohen, A. J.; et al. Estimates and 25-Year Trends of the Global Burden of Disease Attributable to Ambient Air Pollution: An Analysis of Data from the Global Burden of Diseases Study 2015. The Lancet 2017, 389 (10082), 1907-1918.
Combe, R.; et al. The monosodium iodoacetate model of osteoarthritis: a model of chronic nociceptive pain in rats? Neuroscience letters 2004, 370, (2-3), 236-240.
Cooper MA, et al. Fix the antibiotics pipeline. Nature. 2011;472(7341):32-32.
Crofford, L. J., Use of NSAIDs in treating patients with arthritis. Arthritis research & therapy 2013, 15, (3), S2 (10 pages).
Crone S, et al. A novel in Vitro wound biofilm model used to evaluate low-frequency ultrasonic-assisted wound debridement. J Wound Care. 2015;24(2):64-72.
Csafeglobal, The Cost of a Broken Vaccine Cold Chain Part Two, Financial Cost. <http://csafeglobal.com/the-cost-of-a-broken-vaccine-cold-chain-part-two-financial-cost-1> Sep. 17, 2014, 3 pages.
Cui, et al. Study on a piezoelectric micropump for the controlled drug delivery system. Microfluid. Nanofluidics 3, 377-390 (2007).
Curdy, C. et al. Piroxicam delivery into human stratum corneum in vivo: iontophoresis versus passive diffusion. Journal of Controlled Release 2001, 76, (1-2), 73-79.
Curry EJ, et al. Biodegradable nanofiber-based piezoelectric transducer. Proceedings of the National Academy of Sciences. 2020;117(1):214-220.
Curry et al., "Biodegradable piezoelectric force sensor," PNAS, 2018, 115(5):909-914.
Curry, E. J.; et al. 3D nano- and micro-patterning of biomaterials for controlled drug delivery. Therapeutic Delivery 2016.
Da Silva et al., Biocompatibility, biodegradation and excretion of polylactic acid (PLA) in medical implants and theranostic systems. Chem. Eng. J. 340, 9-14 (2018).
Daeschlein G, et al. Antibacterial activity of positive and negative polarity low-voltage pulsed current (LVPC) on six typical Gram-positive and Gram-negative bacterial pathogens of chronic wounds. Wound Repair Regen. 2007;15(3):399-403.
Dagdeviren C, et al. Conformable amplified lead zirconate titanate sensors with enhanced piezoelectric response for cutaneous pressure monitoring. Nature Communications. 2014;5(1):4496.
Dagdeviren C, et al. Conformal piezoelectric energy harvesting and storage from motions of the heart, lung, and diaphragm. Proceedings of the National Academy of Sciences. 2014;111(5):1927.
Dagdeviren et al., "Recent progress in flexible and stretchable piezoelectric devices for mechanical energy harvesting, sensing and actuation," Extreme Mechanics Letters, 2016, 9(1):269-281.
Dai et al., "Electrospun emodin polyvinylpyrrolidone blended nanofibrous membrane: a novel medicated biomaterial for drug delivery and accelerated wound healing," Journal of Materials Science: Materials in Medicine, 2012, 23(11):2709-2716.

(56) References Cited

OTHER PUBLICATIONS

Das, R. et al. Biodegradable Nanofiber Bone-Tissue Scaffold as Remotely-Controlled and Self-Powering Electrical Stimulator. Nano Energy 2020, 105028.
Davidson, C. I.; et al. Airborne Particulate Matter and Human Health: A Review. Aerosol Science and Technology 2005, 39 (8), 737-749.
Degenhart et al., Histological evaluation of a chronically-implanted electrocorticographic electrode grid in a non-human primate. 13, 046019 (2016).
Demiray, "Electro-mechanical remodelling of bones," International Journal of Engineering Science, 1983, 21, (9), 1117-1126.
Derakhshandeh H, et al. A Wirelessly Controlled Smart Bandage with 3D-Printed Miniaturized Needle Arrays. Adv Funct Mater. 2020;30(13):1905544.
Desai, T. A.; et al., Nanoporous implants for controlled drug delivery. In BioMEMS and Biomedical Nanotechnology, Spninger: 2006; pp. 263-286.
Di Mario et al., "Drug-eluting bioabsorbable magnesium stent", 2004, J Interv Cardiol., 17:391-395.
Dimitroulas, T.; et al. In Biologic drugs as analgesics for the management of osteoarthritis, Seminars in arthritis and rheumatism, 2017; Elsevier: pp. 687-691.
Dixon, W. J. et al. A method for obtaining and analyzing sensitivity data. Journal of the American Statistical Association 1948, 43, (241), 109-126.
D'Lima et al. "Implantable sensor technology: measuring bone and joint biomechanics of daily life in vivo", Arthritis Reseasrch and Therapy, 2013, 15: 203.
Dominguez, C. A. et al. Sex differences in the development of localized and spread mechanical hypersensitivity in rats after injury to the infraorbital or sciatic nerves to create a model for neuropathic pain. Gender medicine 2009, 6, 225-234.
Dong P-T, et al. Photolysis of Staphyloxanthin in Methicillin-Resistant *Staphylococcus aureus* Potentiates Killing by Reactive Oxygen Species. Advanced Science. 2019;6(11):1900030.
Donnelly, R. F.; et al. Hydrogel-forming microneedle arrays for enhanced transdermal drug delivery. Advanced functional materials 2012, 22, (23), 4879-4890.
Draize, J. H. et al. Methods for the study of irritation and toxicity of substances apphed topically to the skin and mucous membranes. Journal of pharmacology and Experimental Therapeutics 1944, 82, (3), 377-390.
Dwyer DJ, et al. Antibiotics induce redox-related physiological alterations as part of their lethality. Proceedings of the National Academy of Sciences of the United States of America. 2014;111(20):E2100-2109.
Englander L, et al. Nitric oxide nanoparticle technology: a novel antimicrobial agent in the context of current treatment of skin and soft tissue infection. J Clin Aesthet Dermatol. 2010;3(6):45-50.
Eppley BL, et al. Degradation characteristics of PLLA-PGA bone fixation devices. The Journal of craniofacial surgery. 1997;8(2):116-120.
Esposito S, et al. Antimicrobial Treatment of *Staphylococcus aureus* in Patients With Cystic Fibrosis. Front Pharmacol. 2019;10:849-849.
European Patent Office Extended Search Report for Application No. 18767093.0 dated Nov. 27, 2020 (13 pages).
European Patent Office Extended Search Report for Application No. 19764864 dated Mar. 22, 2022 (11 pages).
European Patent Office Partial Search Report for Application No. 19764864 dated Dec. 21, 2021 (12 pages).
Ewald et al., "Monitoring of vital signs for long-term survival of mice under anesthesia", 2011, Cold Spring Harb Protoc. 2011:pdb.prot5563.
Farah et al. Physical and mechanical properties of PLA, and their functions in widespread applications—a comprehensive review. Adv. Drug Deliv. Rev. 107, 367-392 (2016).
FDA. N95 Respirators, Surgical Masks, and Face Masks. https://www.fda.gov/medical-devices/personal-protective- equipment-infection-control/n95-respirators-surgical-masks-face-masks-and-barrier-face-coverings Last updated July 19, 2022 (6 pages).
Feng, Y. et al. Engineering Spherical Lead Zirconate Titanate to Explore the Essence of Piezo-Catalysis. Nano Energy 2017, 40, 481-486.
Feng, Y.; et al. Self-Powered Electrostatic Filter with Enhanced Photocatalytic Degradation of Formaldehyde Based on Built-in Triboelectric Nano generators. ACS nano 2017, 11 (12), 12411-12418.
Ferreira et al., "Bone Collagen Role in Piezoelectric Mediated Remineralization," Acta Microscopica, 2009, 18(3):278-286.
Formenti, D.; et al. Thermal imaging of exercise-associated skin temperature changes in trained and untrained female subjects. Annals of biomedical engineering 2013, 41, (4), 863-871.
Fosslien, E., Adverse effects of nonsteroidal anti-inflammatory drugs on the gastrointestinal system. Annals of Clinical & Laboratory Science 1998, 28, (2), 67-81.
Foti JJ, et al. Oxidation of the Guanine Nucleotide Pool Underhes Cell Death by Bactericidal Antibiotics. Science. 2012;336(6079):315-319.
Freeman J, et al. Comparison of the efficacy of ramoplanin and vancomycin in both in vitro and in vivo models of clindamycin-induced Clostridium difficile infection. J Antimicrob Chemother. 2005;56(4):717-725.
Friebe, M.; et al. Synovial distribution of "systemically" administered acetylsalicylic acid in the isolated perfused equine distal limb. BMC veterinary research 2013, 9, (1), 56.
Frim, J. et al. Body composition and skin temperature variation. Journal of Applied Physiology 1990, 68, (2), 540-543.
Fu, C.-H. J. et al. Method for determination of aspirin and salicylic acid in rat whole blood by high pressure liquid chromatography. Analytical Letters 1985, 18, (3), 269-277.
Fukada, "New Piezoelectric polymers" 1998, Jpn J Appl Phys 37:2775-2780.
Gabriel D, et al. A photo-triggered layered surface coating producing reactive oxygen species. Biomaterials. 2013;34(38):9763-9769.
Gao, Q., et al. Ultrasound Stimulation of Different Dental Stem Cell Populations: Role of Mitogen-activated Protein Kinase Signaling. J. Endod. 42, 2016, 425-431.
Gentile, P. et al. An overview of poly (lactic-co-glycolic) acid (PLGA)-based biomaterials for bone tissue engineering. International journal of molecular sciences 2014, 15, (3), 3640-3659.
Gibaldi, M. et al. Bioavailability of aspirin from commercial suppositories. Journal of pharmaceutical sciences 1975, 64, (6), 1064-1066.
Glazner et al., "Cost of vaccine administration among pediatric practices," Pediatrics, 2009, 124(Supplement 5):S492-S498.
Gohil, S. V. et al. Spatially controlled rhBMP-2 mediated calvarial bone formation in a transgenic mouse model. International journal of biological macromolecules 2018, 106, 1159-1165.
Golabchi et al., Melatonin improves quality and longevity of chronic neural recording. 180, 225-239 (2018).
Gottlieb, H. E.; et al. Nmr Chemical Shifts of Common Laboratory Solvents as Trace Impurities. Journal of Organic Chemistry 1997, 62 (21), 7512-7515.
Graf et al., "In Stimulation of bone growth by implanted FEP electrets and PVDF piezoelectric films," Proceedings 5th International Symposium on Electrets (ISE 5), Heidelberg, 1985, pp. 813-818.
Grant SS, et al. Eradication of bacterial persisters with antibiotic-generated hydroxyl radicals. Proceedings of the National Academy of Sciences. 2012;109(30):12147.
Grassi, M.; et al. Mathematical modelling and controlled drug delivery: matrix systems. Current drug delivery 2005, 2,(1), 97-116.
Gu, G. Q. et al. Triboelectric Nanogenerator Enhanced Nanofiber Air Filters for Efficient Particulate Matter Removal. Acs Nano 2017, 11 (6), 6211-6217.
Guerin et al., Control of piezoelectricity in amino acids by supramolecular packing. Nat. Mater. 17, 180-186 (2018).

(56) References Cited

OTHER PUBLICATIONS

Guo et al., "Measurements of piezoelectric coefficient d33 of lead zirconate titanate thin films using a mini force hammer", 2013, J Vib Accoust, 135:011003.

Guo, H.; et al. A pure zinc membrane with degradability and osteogenesis promotion for guided bone regeneration: in vitro and in vivo studies. Acta Biomater. 2020, 396-409.

Gurung, D. et al. Transient temperature distribution in human dermal part with protective layer at low atmospheric temperature. International Journal of Biomathematics 2010, 3, (04), 439-451.

Gustafsson, M. et al. Pain, coping and analgesic medication usage in rheumatoid arthritis patients. Patient education and counseling 1999, 37, (1), 33-41.

Gutarowska, B., et al. "PLA nonwovens modified with poly (dimethylaminoethyl methacrylate) as antimicrobial filter materials for workplaces." Textile Research Journal 85.10 (2015): 1083-1094.

Habibovic, "Strategic directions in osteoinduction and biomimetics," Tissue Engineering Part A, 2017, 23, (23-24), 1295-1296.

Hasuike A, et al. In vivo bone regenerative effect of low-intensity pulsed ultrasound in rat calvarial defects. Oral Surgery, Oral Medicine, Oral Pathology, Oral Radiology, and Endodontology. 2011;111(1):e12-e20.

He, M. et al. Intradermal implantable PLGA microneedles for etonogestrel sustained release. Journal of Pharmaceutical Sciences 2020, 1958-1966.

He, Z. et al. An overview of hydrogel-based intra-articular drug delivery for the treatment of osteoarthritis. Colloids and Surfaces B: Biointerfaces 2017, 154, 33-39.

Hickey, D.J., et al. Electrophoretic deposition of MgO nanoparticles imparts antibacterial properties to poly-L-lactic acid for orthopedic applications. Journal of Biomedical Materials Research Part A, 2017, 105(11), 3136-3147.

Hong K-S, et al. Piezoelectrochemical Effect: A New Mechanism for Azo Dye Decolorization in Aqueous Solution through Vibrating Piezoelectric Microfibers. The Journal of Physical Chemistry C. 2012;116(24):13045-13051.

Horodyckid et al., Safe long-term repeated disruption of the blood-brain barrier using an implantable ultrasound device: A multiparametric study in a primate model. J. Neurosurg. 126, 1351-1361 (2017).

Hossain, E.; et al. Recharging and Rejuvenation of Decontaminated N95 Masks. Physics of Fluids 2020, 32 (9), 093304.

Howard, J.; et al, An Evidence Review of Face Masks against Covid-19. Proceedings of the National Academy of Sciences 2021, 118 (4).

Hu H, et al. Stretchable ultrasonic transducer arrays for three-dimensional imaging on complex surfaces. Science Advances. 2018;4(3):eaar3979.

Huang, X.; et al. On the importance and mechanisms of burst release in matrix-controlled drug delivery systems. Journal of controlled release 2001, 73, (2-3), 121-136.

Hui J, et al. Photo-Disassembly of Membrane Microdomains Revives Conventional Antibiotics against MRSA. Advanced Science. 2020;7(6):1903117.

Iati, M. More Experts Now Recommend Medical Masks. Good Ones are Hard to Find. Feb. 2, 2021. https://www.washingtonpost.com/health/2021/02/02/medical-mask-shortage/ (4 pages).

IDATA Reasearch. 2017 US Dental Barrier Membrane Market Driven by Increased Use of Resorbable Membranes. https://idataresearch.com/2017-us-dental-barrier-membrane-market-driven-increased-use-resorbable-membranes/. Nov. 10, 2017. (6 pages).

Idbaih et al., Safety and feasibility of repeated and transient blood-brain barrier disruption by pulsed ultrasound inpatients with recurrent glioblastoma. Clin. Cancer Res. 25, 3793-3801 (2019).

Ikada et al. Enhancement of bone formation by drawn poly(L-lactide). J. Biomed. Mater. Res. 30, 553-558 (1996).

Indian Office Action for Application 202037042930 dated Jun. 20, 2022 (6 pages).

Institute of Medicine of the National Academies. Characteristics of Respirators and Medical Masks. In Reusability of Facemasks During an Influenza Pandemic: Facing the Flu, 2006; pp. 22-42.

International Preliminary Report on Patentability for Application No. PCT/US2018/022441 dated Sep. 17, 2019 (10 pages).

International Preliminary Report on Patentability for Application No. PCT/US2021/021677 dated Sep. 6, 2022 (11 pages).

International Search Report and Written Opinion for Application No. PCT/US2018/022441 dated Aug. 1, 2018 (12 pages).

International Search Report and Written Opinion for Application No. PCT/US2019/020838 dated Jun. 26, 2019 (14 pages).

International Search Report and Written Opinion for Application No. PCT/US21/53887 dated Jan. 28, 2022 (14 pages).

Jacobi, U. et al. Porcine ear skin: an in vitro model for human skin. Skin Research and Technology 2007, 13, (1), 19-24.

Jayson et al, "Intra-articular pressure in rheumatoid arthritis of the knee 3. Pressure changes during joint use", Ann Rheum Dis, 1970, 29:401-408.

Ji, W. et al. Incorporation of stromal cell-derived factor-1α in PCL/gelatin electrospun membranes for guided bone regeneration. Biomaterials 34, 735-745 (2013).

Jung, Y.-s. et al. Thermo-sensitive injectable hydrogel based on the physical mixing of hyaluronic acid and Pluronic F-127 for sustained NSAID delivery. Carbohydrate polymers 2017, 156, 403-408.

Jüni, P.; et al. Intra-articular corticosteroid for knee osteoarthritis. Cochrane Database of Systematic Reviews 2015, (10) (81 pages).

Kang et al., "Bioresorbable silicon electronic sensors for the brain", Nature, 2016, 530:71-76.

Kaushik, S. et al. Lack of pain associated with microfabricated microneedles. Anesthesia & Analgesia 2001, 92, (2), 502-504.

Kean, T.; et al. Biodegradation, Biodistribution and Toxicity of Chitosan. Advanced drug delivery reviews 2010, 62 (1), 3-11.

Kern, H., et al. Recovery of long-term denervated human muscles induced by electrical stimulation. Muscle & nerve 31, 98-101 (2005).

Khalid, B.; et al., Direct Blow-Spinning of Nanofibers on a Window Screen for Highly Efficient Pm2. 5 Removal. Nano letters 2017, 17 (2), 1140-1148.

Khanal, M.; et al. Injectable nanocomposite analgesic delivery system for musculoskeletal pain management. Acta biomaterialia 2018, 74, 280-290.

Kim, D.-H. et al. Sustained release of dexamethasone from hydrophilic matrices using PLGA nanoparticles for neural drug delivery. Biomaterials 2006, 27, (15), 3031-3037.

Kinoshita, N. et al. Noninvasive localized delivery of Herceptin to the mouse brain by MRI-guided focused ultrasound-induced bloodbrain barrier disruption. Proc. Natl. Acad. Sci. U.S.A. 103, 11719-11723 (2006).

Klosterhoff et al., "Implantable Sensors for Regenerative Medicine", Journal of Biomechanical Engineering, ASME Feb. 2017, vol. 139, 021009-1.

Kloth, L. C. Electrical stimulation for wound healing: a review of evidence from in vitro studies, animal experiments, and clinical trials. The international journal of lower extremity wounds 4, 23-44 (2005).

Kobayashi, et al. Label-free imaging of melanoma with confocal photothermal microscopy: Differentiation between malignant and benign tissue. Bioeng. 5, 67 (2018) (18 pages).

Kohanski MA, et al. A Common Mechanism of Cellular Death Induced by Bactericidal Antibiotics. Cell. 2007;130(5):797-810.

Kozai et al., Chronic tissue response to carboxymethyl cellulose based dissolvable insertion needle for ultra-small neural probes. 35, 9255-9268 (2014).

Krasowska A, et al. How microorganisms use hydrophobicity and what does this mean for human needs? Front Cell Infect Microbiol. 2014;4:112-112.

Kullenberg, B. et al. Intraarticular corticosteroid injection: pain relief in osteoarthritis of the hip? The Journal of rheumatology 2004, 31, (11), 2265-2268.

Latimer, J. M. et al. Microwave Oven Irradiation as a Method for Bacterial Decontamination in a Clinical Microbiology Laboratory. Journal of Clinical Microbiology 1977, 6 (4), 340-342.

Laurencin et al., "Bone graft substitutes," Expert Review of Medical Devices, 2006, 3(1):49-57.

Laurencin et al., "Regenerative engineering," Science translational medicine, 2012, 4(160): 160ed9, 4 pages.

(56) References Cited

OTHER PUBLICATIONS

Laurencin et al., "Tissue engineering: orthopedic applications," Annual review of biomedical engineering, 1999, 1, (1), 19-46.
Laurencin, C. T.; et al. Delivery of small molecules for bone regenerative engineering: preclinical studies and potential clinical applications. Drug discovery today 2014, 19, (6), 794-800.
Leatherby, L. As Covid Cases Rise All over U.S., Lower Vaccination Rates Point to Worse Outcomes. Jul. 31, 2021. https://www.nytimes.com/interactive/2021/07/31/us/covid-delta-cases-deaths.html?action=click&module=Spotlight&pgtype=Homepage (3 pages).
Lee et al., "Micromachined piezoelectric force senors based on PZT thin films", 1996, IEEE Trans Ultrason Farroelectri Freq Control, 43:553-559.
Lee et al., Lactic acid assisted fabrication of bioactive three-dimensional PLLA/β-TCP fibrous scaffold for biomedical application. Chem. Eng. J. 347, 771-781 (2018).
Lee, et al. Piezoelectric properties of electrospun poly(L-lactic acid) nanofrber web. Mater. Lett. 148, 58-62 (2015).
Leung, L. et al. Comparison of morphology and mechanical properties of PLGA bioscaffolds. Biomedical Materials 2008, 3, (2), 025006.
Lewin et al., Free serum haemoglobin is associated with brain atrophy in secondary progressive multiple sclerosis. Wellcome Open Res. 1, 10 (2016) (23 pages).
Lewftus, S. et al. The Effect of Nanoclays on the Properties of PLLA-modified Polymers Part 1: Mechanical and Thermal Properties. Journal of Polymers and the Environment 14, 171-177 (2006).
Li J, et al. Evaluation of Ultrasound-Induced Damage to *Escherichia coli* and *Staphylococcus aureus* by Flow Cytometry and Transmission Electron Microscopy. Appl Environ Microbiol. 2016;82(6):1828-1837.
Li Z, et al. Using Positively Charged Magnetic Nanoparticles to Capture Bacteria at Ultralow Concentration. Nanoscale Research Letters. 2019;14(1):195 (8 pages).
Li, C. et al. Dual-mode operation of flexible piezoelectric polymer diaphragm for intracranial pressure measurement. Appl. Phys. Lett. 96, 053502 (2010).
Li, H. et al. Enhancing the Mechanical Properties of Electrospun Nanofiber Mats through Controllable Welding at the Cross Points. Macromolecular rapid communications 2017, 38 (9), 1600723.
Li, N.; et al. A Work Group Report on Ultrafine Particles (American Academy of Allergy, Asthma & Immunology): Why Ambient Ultrafine and Engineered Nanoparticles Should Receive Special Attention for Possible Adverse Health Outcomes in Human Subjects. Journal of Allergy and Clinical Immunology 2016, 138 (2), 386-396.
Li, P. et al. Air Filtration in the Free Molecular Flow Regime: A Review of High-Efficiency Particulate Air Filters Based on Carbon Nanotubes. Small 2014, 10 (22), 4543-4561.
Li, P. et al. Apatite formation induced by silica gel in a simulated body fluid. Journal of the American Ceramic Society 1992, 75, (8), 2094-2097.
Li, Q. et al. Involvement of the spinal NALP1 inflammasome in neuropathic pain and aspirin-triggered-15-epi-lipoxin A4 induced analgesia. Neuroscience 2013, 254, 230-240.
Li, W. et al. Rapidly separable microneedle patch for the sustained release of a contraceptive. Nature Biomedical Engineering 2019, 3, (3), 220-229.
Li, W.; et al. Long-acting reversible contraception by effervescent microneedle patch. Science advances 2019, 5, (11), eaaw8145.
Liao, L.; et al. Can N95 Respirators Be Reused after Disinfection? How Many Times? ACS nano 2020, 14 (5), 6348-6356.
Liu et al., "Design and development of three-dimensional scaffolds for tissue engineering", 2007, Chem Eng Res Des, 85:1051-1064.
Liu, C.; et al. Transparent Air Filter for High-Efficiency Pm 2.5 Capture. Nature communications 2015, 6 (1), 1-9.
Liu, G. et al. Self-Powered Electrostatic Adsorption Face Mask Based on a Triboelectric Nanogenerator. ACS applied materials & interfaces 2018, 10 (8), 7126-7133.

Liu, H. et al. High-Performance Pm0. 3 Air Filters Using Self-Polarized Electret Nanofiber/Nets. Advanced Functional Materials 2020, 30 (13), 1909554.
Liu, X. et al. A biodegradable multifunctional nanofibrous membrane for periodontal tissue regeneration. Acta Biomater. 2020, 108, 207-222.
Liu, Z.; et al. Understanding the Factors Involved in Determining the Bioburdens of Surgical Masks. Annals of translational medicine 2019, 7 (23).
Lo, K. et al. Small-molecule based musculoskeletal regenerative engineering. Trends in biotechnology 2014, 32, (2), 74-81.
Lobritz MA, et al. Antibiotic efficacy is linked to bacterial cellular respiration. Proceedings of the National Academy of Sciences of the United States of America. 2015;112(27):8173-8180.
Long Y, et al. Effective Wound Healing Enabled by Discrete Alternative Electric Fields from Wearable Nanogenerators. ACS Nano. 2018;12(12):12533-12540.
Lops, C.; et al. Sonophotocatalytic Degradation Mechanisms of Rhodamine B Dye Via Radicals Generation by Micro-and Nano-Particles of Zno. Applied Catalysis B: Environmental 2019, 243, 629-640.
Lu, W.-C. et al. Effect of magnesium on the osteogenesis of normal human osteoblasts. Magnes. Res. 30, 42-52 (2017).
Lu, X.; et al. Theoretical analysis of calcium phosphate precipitation in simulated body fluid. Biomaterials 2005, 26,(10), 1097-1108.
Ludwig, The velocity of sound through tissues and the acoustic impedance of tissues. The journal of the acoustical society of America 22, 862-866 (1950).
Lundgren, D., et al. "The use of a new bioresorbable barrier for guided bone regeneration in connection with implant installation. Case reports." Clinical Oral Implants Research 5.3 (1994): 177-184.
Luque-Agudo V, et al. Aging of Solvent-Casting PLA-Mg Hydrophobic Films: Impact on Bacterial Adhesion and Viability. Coatings. 2019;9(12) 814.
Lv, D.; et al. Ecofriendly Electrospun Membranes Loaded with Visible-Light-Responding Nanoparticles for Multifunctional Usages: Highly Efficient Air Filtration, Dye Scavenging, and Bactericidal Activity. ACS applied materials & interfaces 2019, 11 (13), 12880-12889.
Madlon-Kay et al., "Too many shots? Parent, nurse, and physician attitudes toward multiple simultaneous childhood vaccinations," Archives of Family Medicine, 1994, 3(7):610-13.
Mahdavi, A. et al. Particle Loading Time and Humidity Effects on the Efficiency of an N95 Filtering Facepiece Respirator Model under Constant and Inhalation Cyclic Flows. Annals of Occupational Hygiene 2015, 59 (5), 629-640.
Maloney et al., "Intracranial pressure monitoring in acute liver failure: Institutional case series", 2016, Neurocrit Care 25:86-93.
Manoukian, M. A. C. et al. Topical administration of ibuprofen for injured athletes: considerations. formulations, and comparison to oral delivery. Sports medicine-open 2017, 3, (1), 36, 1-9.
Marzoli, F. et al. Long-lasting, antinociceptive effects of pH-sensitive niosomes loaded with ibuprofen in acute and chronic models of pain. Pharmaceutics 2019, 11, (2), 62, 1-12.
McCrudden, M. T. et al. Design and physicochemical characterisation of novel dissolving polymeric microneedle arrays for transdermal delivery of high dose, low molecular weight drugs. Journal of Controlled Release 2014, 180, 71-80.
McDannold, et al. MRI-guided targeted blood-brain barrier disruption with focused ultrasound: Histological findings in rabbits. Ultrasound Med. Biol. 31, 1527-1537 (2005).
McHugh et al., "Single-injection vaccines: Progress, challenges, and opportunities," Journal of Controlled Release, 2015, 219:596-609.
Meng et al., "A Hybrid Inductive-Ultrasonic Link for Wireless Power Transmission to Millimeter-Sized Biomedical Implats," IEEE Transactions on Circuits and Systems—II: Express Briefs, 2017, 64(10): 1137-1141.
Meylan S, et al. Targeting Antibiotic Tolerance, Pathogen by Pathogen. Cell. 2018;172(6):1228-1238.
Middleton, J. C.; Tipton, A. J., Synthetic Biodegradable Polymers as Orthopedic Devices. Biomaterials 2000, 21 (23), 2335-2346.

(56) References Cited

OTHER PUBLICATIONS

Mihai MM, et al. Nanomaterials for Wound Healing and Infection Control. Materials (Basel). 2019;12(13):2176.

Minary-Jolandan et al., "Nanoscale characterization of isolated individual type I collagen fibrils: Polarization and piezoelectricity", 2009, Nanotechnology 20:085706.

Moga, K. A. et al. Rapidly-dissolvable microneedle patches via a highly scalable and reproducible soft lithography approach. Advanced Materials 2013, 25, (36), 5060-5066.

Mohseni et al., "Gellan gel comprising short PVDF based-nanofibers: The effect of piezoelectric nanofiber on the mechanical and electrical behavior," Materialstoday Communications, vol. 26, Mar. 2021, 101785.

Monsen T, et al. In Vitro Effect of Ultrasound on Bacteria and Suggested Protocol for Sonication and Diagnosis of Prosthetic Infections. J Clin Microbiol. 2009;47(8):2496-2501.

Morel CM, et al. Stoking the antibiotic pipeline. BMJ. 2010;340:1115-1118.

Nair, L. S.; et al. Polymers as biomaterials for tissue engineering and controlled drug delivery. In Tissue engineering I, Springer: 2005; pp. 47-90.

Najdovski, L. et al. The Killing Activity of Microwaves on Some Non-Sporogenic and Sporogenic Medically Important Bacterial Strains. Journal of Hospital Infection 1991, 19 (4), 239-247.

Narayanan et al., "Poly (lactic acid)-based biomaterials for orthopaedic regenerative engineering," Advanced drug delivery reviews, 2016, 107, 247-276.

Nasajpour, A. et al. A multifunctional polymeric periodontal membrane with osteogenic and antibacterial characteristics. Adv. Funct. Mater. 28, 1703437 (2018).

Nazir, M. A. Prevalence of periodontal disease, its association with systemic diseases and prevention. International journal of health sciences 11, 72 (2017), 72-80.

Neely RM, et al. Recent advances in neural dust: towards a neural interface platform. Current Opinion in Neurobiology. 2018;50:64-71.

Nguyen et al., "Piezoelectric nanonribbons for monitoring cellular deformations," Nature Nanotechnology, 2012, 7:587-593.

Nguyen et al., "Wafter-scale nanopatterning and translation into high-performance piezoelectric nanowires", 2010, Nano Lett 10: 4595-4599.

Nguyen, "A novel injectable piezoelectric hydrogel for osteoarthritis treatment," NIH Project No. 1R21AR074645-01, Award notice date: Apr. 23, 2019, Project Start Date: Jun. 1, 2019 <https://reporter.nih.gov/project-details/9651964> (3 pages).

Nguyen, et al., "Bionics in tissue engineering" 2017, Tissue Engineering for Artifical Organs, pp. 677-669.

Nicosia, A., et al. "Air filtration and antimicrobial capabilities of electrospun PLA/PHB containing ionic liquid." Separation and Purification Technology 154 (2015): 154-160.

Noguchi, Y. Why N95 Masks are Stil in Short Supply in the U.S. https://www.npr.org/sections/health-shots/2021/01/27/960336778/why-n95-masks-are-still-inshort-supply-in-the-u-s, Jan. 27, 2021 (17 pages).

Norman, J. J.; et al. Microneedle patches: usability and acceptability for self-vaccination against influenza. Vaccine 2014, 32, (16), 1856-1862.

Novotny et al. Molybdenum intake influences molybdenum kinetics in men. J. Nutr. 137, 37-42 (2007).

O'Dowd et al., "Face Masks and Respirators in the Fight Against the COVID-19 Pandemic: A Review of Current Materials, Advances and Future Perspectives," Materials 2020, 13(15), 3363.

Olatunji, O.; et al. Microneedle-assisted transdermal delivery of acetylsalicylic acid (aspirin) from biopolymer films extracted from fish scales. Polymer Bulletin 2018, 75, (9), 4103-4115.

Omidinia-Anarkoli, A.; et al. An Injectable Hybrid Hydrogel with Oriented Short Fibers Induces Unidirectional Growth of Functional Nerve Cells. Small 2017, 13, (36).

Padilla F, et al. Stimulation of bone repair with ultrasound: A review of the possible mechanic effects. Ultrasonics. 2014;54(5):1125-1145.

Panieri E, et al. ROS signaling and redox biology in endothelial cells. Cell Mol Life Sci. 2015;72(17):3281-3303.

Pankey GA, et al. Clinical relevance of bacteriostatic versus bactericidal mechanisms of action in the treatment of Gram-positive bacterial infections. Clin Infect Dis. 2004;38(6):864-870.

Park, J.-H. et al. Biodegradable polymer microneedles: fabrication, mechanics and transdermal drug delivery. Journal of controlled release 2005, 104, (1), 51-66.

Patel et al., "Development of a Sonically Powered Biodegradable Nanogenerator for Bone Regeneration", 2019, University of Connecticut, 46 pages.

Pathak, R. K. et al. A nanoparticle cocktail: temporal release of predefined drug combinations. Journal of the American Chemical Society 2015, 137, (26), 8324-8327.

Patrick, J.; et al. A randomized trial to assess the pharmacodynamics and pharmacokinetics of a single dose of an extended-release aspirin formulation. Postgraduate medicine 2015, 127, (6), 573-580.

Paul, et al. Novel 3D analysis of Claudin-5 reveals significant endothelial heterogeneity among CNS microvessels. 86, 1-10 (2013).

Pavel A, et al. Prophylactic Antibiotics in Clean Orthopaedic Surgery. JBJS. 1974;56(4):777-782.

Pelletier, J.-P.; et al. In Efficacy and safety of oral NSAIDs and analgesics in the management of osteoarthritis: Evidence from real-life setting trials and surveys, Seminars in arthritis and rheumatism, 2016; Elsevier: pp. S22-S27.

Peltoniemi et al. SR-PLLA and SRPGA miniscrews: Biodegradation and tissue reactions in the calvarium and dura mater. J. Craniomaxillofac. Surg. 27, 42-50 (1999).

Peng, X., et al. "A breathable, biodegradable, antibacterial, and self-powered electronic skin based on all-nanofiber triboelectric nanogenerators." Science Advances 6.26 (2020): eaba9624.

Peterson RV, et al. The effect of frequency and power density on the ultrasonically-enhanced killing of biofilm-sequestered *Escherichia coli*. Colloids and Surfaces B: Biointerfaces. 2000;17(4):219-227.

Poeggel et al., "Optical Fibre Pressure Sensors in Medical Applications," Sensors, 2015, 15(7): 17115-17148.

Prausnetz, M. R. Engineering microneedle patches for vaccination and drug delivery to skin. Annual review of chemical and biomolecular engineering 2017, 8, 177-200.

Prokuski L. Prophylactic Antibiotics in Orthopaedic Surgery. JAAOS—Journal of the American Academy of Orthopaedic Surgeons. 2008;16(5):283-293.

Qi et al., "Enhanced piezoelectricity and stretchability in energy harvesting devices fabricated from buckled PZT ribbons", 2011, Nano Lett. 11:1331-1336.

Qi et al., "Stretchable piezoelectric nanoribbons for biocompatible energy harvesting", Stretchable Electrionics, pp. 111-139, 2013.

Qian, Y. et al. Performance of N95 Respirators: Filtration Efficiency for Airborne Microbial and Inert Particles. American Industrial Hygiene Association Journal 1998, 59 (2), 128-132.

Qiu, Y. et al. Enhancement of skin permeation of docetaxel: a novel approach combining microneedle and elastic liposomes. Journal of Controlled Release 2008, 129, (2), 144-150.

Quinn, H. L. et al. Design of a dissolving microneedle platform for transdermal delivery of a fixed-dose combination of cardiovascular drugs. Journal of pharmaceutical sciences 2015, 104, (10), 3490-3500.

Ramadan et al., "A review of piezoelectric polymers as functional materials for electromechanical transducers," Smart Materials and Structures 23, 2014, 033001.

Ratajska, M. et al. Studies on the Biodegradation of Chitosan in an Aqueous Medium. Fibres & Textiles in Eastern Europe 2003, (3 (42)), 75-79.

Raynor, P. C. et al. The Long-Term Performance of Electrically Charged Filters in a Ventilation System. Journal of occupational and environmental hygiene 2004, 1 (7), 463-471.

Riggin, C. N.; et al. Intra-articular tibiofemoral injection of a nonsteroidal anti-inflammatory drug has no detrimental effects on joint mechanics in a rat model. Journal of Orthopaedic Research 2014, 32, (11), 1512-1519.

(56) References Cited

OTHER PUBLICATIONS

Ripolin, A.; et al. Successful application of large microneedle patches by human volunteers. International journal of pharmaceutics 2017, 521, (1-2), 92-101.

Rizzello L, et al. Nanotechnology tools for antibacterial materials. Nanomedicine (Lond). 2013;8(5):807-821.

Roberts, M. S. et al. Percutaneous absorption of topically apphed NSAIDS and other compounds: role of solute properties, skin physiology and delivery systems. Inflammopharmacology 1999, 7, (4), 339.

Robertson JMC, et al. A comparison of the effectiveness of TiO2 photocatalysis and UVA photolysis for the destruction of three pathogenic micro-organisms. Journal of Photochemistry and Photobiology A: Chemistry. 2005;175(1):51-56.

Rohrer, M. D. et al. Microwave Sterilization. Journal of the American Dental Association (1939) 1985, 110 (2), 194-198.

Rolland et al., "Direct fabrication and harvesting of monodisperse, shape-specific nanobiomaterials," Journal of the American Chemical Society, 2005, 127(28):10096-10100.

Roy S, et al. Disposable Patterned Electroceutical Dressing (PED-10) is Safe for Treatment of Open Clinical Chronic Wounds. Advances in Wound Care. 2019;8(4):149-159.

Ru et al., "Dominant B-form of poly(l-lactic acid) obtained directly from melt under shear and pressure fields", 2016, Macromolecules 49:3826-3837.

Runyan CM, et al. Low-frequency ultrasound increases outer membrane permeability of Pseudomonas aeruginosa. The Journal of General and Applied Microbiology. 2006;52(5):295-301.

Ruparelia JP, et al. Strain specificity in antimicrobial activity of silver and copper nanoparticles. Acta Biomater. 2008;4(3):707-716.

Russell, R., Non-steroidal anti-inflammatory drugs and gastrointestinal damage—problems and solutions. Postgraduate medical journal 2001, 77, (904), 82-88.

Sadorsky, P., The Effect of Urbanization and Industrialization on Energy Use in Emerging Economies: Implications for Sustainable Development. American Journal of Economics and Sociology 2014, 73 (2), 392-409.

Salomoni R, et al. Antibacterial effect of silver nanoparticles in Pseudomonas aeruginosa. Nanotechnol Sci Appl. 2017;10:115-121.

Sanni et al., "Inductive and Ultrasonic Multi-Tier Interface for Low-Power, Deeply Implantable Medical Devices," IEEE Transactions on Biomedical Circuits and Systems, 2012, 6(4):297-308.

Santora, M. et al. Covid Updates: Known Global Tool Reaches 200 Millions Virus Infections. Aug. 4, 2021. https://web.archive.org/web/20210804234532/https://www.nytimes.com/live/2021/08/04/world/covid-delta-variant-vaccine (21 pages).

Saravanos et al., "Layerwise mechanics and finite element for the dynamic analysis of piezoelectric composite plates", 1997, Int J Solids Struct 34:359-378.

Sawano et al., "New design of actuator using shear piezoelectricity of a chiral polymer, and prototype device", 2010, Polym. Int. 59: 365-370.

Schlesinger, E. et al. Polycaprolactone thin-film drug delivery systems: empirical and predictive models for device design. Materials Science and Engineering: C 2015, 57, 232-239.

Schlesinger, E.; et al. A tunable, biodegradable, thin-film polymer device as a long-acting implant delivering tenofovir alafenamide fumarate for HIV pre-eXposure prophylaxis. Pharmaceutical research 2016, 33, (7), 1649-1656.

Schmook, F. P.; et al. Comparison of human skin or epidermis models with human and animal skin in in-vitro percutaneous absorption. International journal of pharmaceutics 2001, 215, (1-2), 51-56.

Sencadas et al., Local piezoelectric activity of single poly(L-lactic acid) (PLLA) microfibers. Appl. Phys. A 109, 51-55 (2012).

Seol et al., "Hysteretic behavior of contact force response in triboelectric nanogenerator", 2017, Nano Energy 32:408-413.

Seth AK, et al. Noncontact, low-frequency ultrasound as an effective therapy against Pseudomonas aeruginosa—infected biofilm wounds. Wound Repair Regen. 2013;21(2):266-274.

Shah SR, et al. Evolving strategies for preventing biofilm on implantable materials. Materials Today. 2013;16(5):177-182.

Shah, S.; et al. Controversies and advances in non-steroidal anti-inflammatory drug (NSAID) analgesia in chronic pain management. Postgraduate medical journal 2012, 88, (1036), 73-78.

Shalumon KT, et al. Sodium alginate/poly(vinyl alcohol)/nano ZnO composite nanofibers for antibacterial wound dressings. Int J Biol Macromol. 2011;49(3):247-254.

Sheets, D.; et al. An Apparatus for Rapid and Nondestructive Comparison of Masks and Respirators. Review of Scientific Instruments 2020, 91 (11), 114101.

Shende et al., Micro to nanoneedles: a trend of modernized transepiderrnal drug delivery system, Artificial Cells, Nanomedicine, and Biotechnology, 2017, 8 pages.

Shim, J.-H. et al. Efficacy of rhBMP-2 loaded PCL/PLGA/β-TCP guided bone regeneration membrane fabricated by 3D printing technology for reconstruction of calvaria defects in rabbit. Biomedical materials 9, 065006 (2014) (9 pages).

Shokri, J.; et al. Swellable elementary osmotic pump (SEOP): an effective device for delivery of poorly water-soluble drugs. European Journal of Pharmaceutics and Biopharmaceutics 2008, 68, (2), 289-297.

Shrivastava S, et al. Characterization of enhanced antibacterial effects of novel silver nanoparticles. Nanotechnology. 2007;18(22):225103 (9 pages).

Shuai et al., "Surface modification enhances interfacial bonding in PLLA/MgO bone scaffold," Materials Science and Engineering: C, vol. 108, Mar. 2020, 110486.

Shuai, C. et al. nMgO-incorporated PLLA bone scaffolds: Enhanced crystallinity and neutralized acidic products. Materials & Design 174, 107801 (2019).

Silva, E.; et al. Pdlla Honeycomb-Like Scaffolds with a High Loading of Superhydrophilic Graphene/Multi-Walled Carbon Nanotubes Promote Osteoblast in Vitro Functions and Guided in Vivo Bone Regeneration. Materials Science and Engineering: C 2017, 73, 31-39.

Simonelli et al., "Dissolution rates of high energy polyvinylpyrrolidone (PVP)-sulfathiazole coprecipitates," Journal of pharmaceutical sciences, 1969, 58(5):538-549.

Sinatra, R. S.; et al. Efficacy and safety of single and repeated administration of 1 gram intravenous acetaminophen injection (paracetamol) for pain management after major orthopedic surgery. Anesthesiology: The Journal of the American Society of Anesthesiologists 2005, 102, (4), 822-831.

Sinderby et al., "Diaphragm activation during exercise in chronic obstructive pulmonary disease", 2001, Am J Respir Crit Care Med, 163:1637-1641.

Smith et al. Direct observation of shear piezoelectricity in poly-L-lactic acid nanowires. APL Mater. 5, 074105 (2017) (8 pages).

Soltman et al., "Inkjet-printed line morphologies and temperature control of the coffee ring effect," Langmuir, 2008, 24(5):2224-2231.

Starr MB, et al. Coupling of piezoelectric effect with electrochemical processes. Nano Energy. 2015; 14:296-311.

Stokes, A.; et al. The contribution of obesity to prescription opioid use in the United States. Pain 2019, 160, (10), 2255.

Subbiahdoss G, et al. Magnetic targeting of surface-modified superparamagnetic iron oxide nanoparticles yields antibacterial efficacy against biofilms of gentamicin-resistant staphylococci. Acta Biomater. 2012;8(6):2047-2055.

Sullivan et al., "Dissolving polymer microneedle patches for influenza vaccination," Nature medicine, 2010, 16(8):915-921.

Sultana et al., Human skin interactive self-powered wearable piezoelectric bio-eskin by electrospun poly-L-lactic acid nanofibers for non-invasive physiological signal monitoring. J. Mater. Chem. B 5, 7352-7359 (2017).

Syuhei et al., "Sensing using piezoelectric chiral polymer fiber", 2012, Jpn. J. Appl. Phys. 51:09LD16.

Szablowski, et al. Acoustically targeted chemogenetics for the non-invasive control of neural circuits. Nat. Biomed. Eng. 2, 475-484 (2018).

Taguchi, V. et al. Determination of drug stability in aspirin tablet formulations by high-pressure liquid chromatography. Journal of pharmaceutical sciences 1981, 70, (1), 64-67.

(56) References Cited

OTHER PUBLICATIONS

Tajitsu et al. Novel tweezers for biological cells using piezoelectric polylactic acid fibers. Ferroelectrics 320, 133-139 (2005).
Tajitsu et al., "Microactuators with piezoelectric polylactic acid fibers—toward the realizaation of tweezers for biological cells", 2004, Ferroelectrics 304:195-200.
Tajitsu, Y. Fundamental study on improvement of piezoelectricity of poly(ι-lactic acid) and its application to film actuators. IEEE Trans. Ultrason. Ferroelectr. Freq. Control 60, 1625-1629 (2013).
Takeuchi, H.; et al. Influence of skin thickness on the in vitro permeabilities of drugs through Sprague-Dawley rat or Yucatan micropig skin. Biological and Pharmaceutical Bulletin 2012, 35, (2), 192-202.
Talmor et al., "Mechanical ventilation guided by esophageal pressure in acute lung injury", N. Engl. J Med., 2008, 359, 2095-2104.
Tams J, et al. Poly(l-lactide) bone plates and screws for internal fixation of mandibular swing osteotomies, Int J Oral Maxillofac Surg. 1996;25(1):20-24.
Tan, et al. Studies on Thermal Decomposition Mechanism and Kinetics of Aspirin [J]. Acta Physico-chimica Sinica 2004, 1m 50-54. With English Abstract.
Tan, G., et al. "Surface-selective preferential production of reactive oxygen species on piezoelectric ceramics for bacterial killing." ACS applied materials & interfaces 8.37 (2016): 24306-24309.
Tanimoto et al., "Effect of helix inversion of poly(β-phenethyl l-aspartate) on macroscopic piezoelectricity," Japanese Journal of Apphed Physics, 2014, 53(9S):09PC01.
Tao H, et al. Silk-based resorbable electronic devices for remotely controlled therapy and in vivo infection abatement. Proceedings of the National Academy of Sciences. 2014; 111(49):17385.
Tezel A, et al. Topical Delivery of Anti-sense Oligonucleotides Using Low-Frequency Sonophoresis. Pharm Res. 2004;21(12):2219-2225.
Thakur, R. R. S.; et al. Microneedle-mediated intrascleral delivery of in situ forming thermoresponsive implants for sustained ocular drug delivery. Journal of Pharmacy and Pharmacology 2014, 66, (4), 584-595.
Thermofisher Scientific. Residual Solvent Analysis Information. Jul. 14, 2019. https://web.archive.org/web/20190714025617/https://www.thermofisher.com/us/en/home/industrial/pharma-biopharma/pharma-biopharma-learning-center/pharmaceutical-qa-qc-information/residual-solvent-analysis-information.html (6 pages).
Timin, A. S., et al. "Multifunctional scaffolds with improved antimicrobial properties and osteogenicity based on piezoelectric electrospun fibers decorated with bioactive composite microcapsules." ACS applied materials & interfaces 10.41 (2018): 34849-34868.
Tran, K. T.; et al. Lithography-based methods to manufacture biomaterials at small scales. Journal of Science: Advanced Materials and Devices 2017, 2, (1), 1-14.
Tucho, G. T.; et al., Universal Use of Face Masks and Related Challenges During Covid-19 in Developing Countries. Risk Management and Healthcare Policy 2021, 14, 511.
Ueki, H.; et al. Effectiveness of Face Masks in Preventing Airborne Transmission of Sars-Cov-Z. MSphere 2020, 5(5), e00637-20.
Ummadi, S.; et al. Overview on controlled release dosage form. System 2013, 7, (8), 51-60.
VAERS, Vaccine Adverse Event Reporting System, <https://vaers.hhs.gov/data/index> webpage available as early as Oct. 9, 2009, 2 pages.
Valentini, R. F., et al. Electrically charged polymeric substrates enhance nerve fibre outgrowth in vitro. Biomaterials 13, 183-190 (1992).
Van Acker H, et al. The Role of Reactive Oxygen Species in Antibiotic-Mediated Killing of Bacteria. Trends in Microbiology. 2017;25(6):456-466.
Vykhodtseva, et al. Progress and problems in the application of focused ultrasound for blood-brain barrier disruption. Ultrasonics 48, 279-296 (2008).
Walmsley, A. et al. Ultrasound in dentistry. Part 2—periodontology and endodontics. J. Dent. 20, 11-17 (1992).

Walsh C. Molecular mechanisms that confer antibacterial drug resistance. Nature. 2000;406(6797):775-781.
Wang Y, et al. Piezo-catalysis for nondestructive tooth whitening. Nature Communications. 2020;11(1):1328.
Wang, C. et al. Enhanced cancer immunotherapy by microneedle patch-assisted delivery of anti-PD1 antibody. Nano letters 2016, 16, (4), 2334-2340.
Wang, C. et al. Silk Nanofibers as High Efficient and Liglilweight Air Filter. Nano Research 2016, 9 (9), 2590-2597.
Wang, N. et al. Tunable Fabrication of Three-Dimensional Polyamide-66 Nano-Fiber/Nets for High Efficiency Fine Particulate Filtration. Journal of Materials Chemistry 2012, 22 (4), 1445-1452.
Wang, P. et al. Ultrasmall Barium Titanate Nanoparticles for Highly Efficient Hypoxic Tumor Therapy Via Ultrasound Triggered Piezocatalysis and Water Splitting. ACS nano 2021, 11326-11340.
Wang, S. et al. Controlled release of levonorgestrel from biodegradable poly (D, L-lactide-co-glycolide) microspheres: in vitro and in vivo studies. International journal of pharmaceutics 2005, 301, (1-2), 217-225.
Wang, S. et al. Electret Polyvinylidene Fluoride Nanofibers Hybridized by Polytetrafluoroethylene Nanoparticles for High-Efficiency Air Filtration. ACS applied materials & interfaces 2016, 8 (36), 23985-23994.
Wang, Z. et al. Porous Bead-on-String Poly (Lactic Acid) Fibrous Membranes for Air Filtration. Journal of colloid and interface science 2015, 441, 121-129.
Wang, Z.-F. et al. Aspirin-triggered Lipoxin A4 attenuates mechanical allodynia in association with inhibiting spinal JAK2/STAT3 signaling in neuropathic pain in rats. Neuroscience 2014, 273, 65-78.
Ward AR, et al. Comparison of Heating of Nonliving Soft Tissue produced by 45 kHz and 1 MHz Frequency Ultrasound Machines. J Orthop Sports Phys Ther. 1996;23(4):258-266.
Wartzek, et al. Triboelectricity in capacitive biopotential measurements. IEEE Trans. Biomed. Eng. 58, 1268-1277 (2011).
WHO. Coronavirus Disease (Covid-19) Advice for the Public: When and How to Use Masks. https://www.who.int/emergencies/diseases/novel-coronavirus-2019/advice-for-public/when-andhow-to-use-masks (Updated Dec. 2021) (12 pages).
WHO. Shortage of Personal Protective Equipment Endangering Health Workers Worldwide. https://www.who.int/news/item/03-03-2020-shortage-of-personal-protective-equipment-endangering-health-workers-worldwide. Mar. 3, 2020 (3 pages).
Wiese, A. D.; et al. Opioid analgesics and the risk of serious infections among patients with rheumatoid arthritis: a self-controlled case series study. Arthritis & rheumatology 2016, 68, (2), 323-331.
Witzleb et al. Exposure to chromium, cobalt and molybdenum from metal-on-metal total hip replacement and hip resurfacing arthroplasty. Acta Orthop. 77, 697-705 (2006).
Woltjer et al. (2016) "Optimization of piezo-MEMS layout for a bladder monitor" in 2016 IEEE International Ultrasonics Symposium (IUS) (IEEE, 2016), pp. 1-4.
Wu, S. et al. Surface Modification of Pure Magnesium Mesh for Guided Bone Regeneration: In Vivo Evaluation of Rat Calvarial Defect. Materials 12, 2684 (2019).
Wynn, R. F. et al. A small proportion of mesenchymal stem cells strongly expresses functionally active CXCR4 receptor capable of promoting migration to bone marrow. Blood 104, 2643-2645 (2004).
Xin et al., A Site-Specific Integrated Col2.3GFP Reporter Identifies Osteoblasts Within Mineralized Tissue Formed In Vivo by Human Embryonic Stem Cells. Stem cells translational medicine 3, 1125-1137 (2014).
Xiong, Z.-C. et al. Flexible Hydroxyapatite Ultralong Nanowire-Based Paper for Highly Efficient and Multifunctional Air Filtration. Journal of Materials Chemistry A 2017, 5 (33), 17482-17491.
Xu et al., "Future of the particle replication in nonwetting templates (PR.INT) technology," Angewandte Chemie International Edition, 2013, 52(26):6580-6589.
Xu et al., "Improvements of thermal property and crystallization behavior of PLLA based multiblock copolymer by forming sterocomplex with PDLA oligomer", 2006, Polymer (Guildf), 47:3922-3928.

(56) References Cited

OTHER PUBLICATIONS

Xu X, et al. Strong vibration-catalysis of ZnO nanorods for dye wastewater decolorization via piezo-electro-chemical coupling. Chemosphere. 2018;193:1143-1148.
Xu, E. G.; et al.Preventing Masks from Becoming the Next Plastic Problem. Frontiers of environmental science & engineering 2021, 15 (6), 125.
Yang, M.; et al. Is Pm1 Similar to Pm2. 5? A New Insight into the Association of Pm1 and Pm2. 5 with Children's Lung Function. Environment International 2020, 145, 106092.
Yoshida et al., "High piezoelectric performance of poly (lactic acid) film manufactured by solid state extrusion", 2014, Jpn. J. Appl. Phys. 53:09PC02.
Yoshida et al., "Piezoelectric motion of multilayer film with alternate rows of optical isomers of chiral polymer film", 2011, Jpn J Appl Phys 50:09ND13.
Yoshimoto, I. et al. Development of layered PLGA membranes for periodontal tissue regeneration. Dent. Mater. 34, 538-550, (2018).
You H., et al. Strong piezo-electrochemical effect of multiferroic BiFeO3 square micro-sheets for mechanocatalysis. Electrochem Commun. 2017;79:55-58.
Yu et al., "Oral fast-dissolving drug delivery membranes prepared from electrospun polyvinylpyrrolidone ultrafine fibers," Nanotechnology, 2009, 20(5):055104, 9 pages.
Yu, J.; et al. Glucose-responsive insulin patch for the regulation of blood glucose in mice and minipigs. Nature Biomedical Engineering 2020, 1-8.
Yu, Y. et al. Multifunctions of dual Zn/Mg ion co-implanted titanium on osteogenesis, angiogenesis and bacteria inhibition for dental implants. Acta Biomater. 49, 590-603 (2017).
Zhang et al., "Piezoelectric polymer multilayer on flexible substrate for energy harvesting," IEEE Transactions on Ultrasonics, Ferroelectrics, and Frequency Control, 2013, 60(9):2013-2020.
Zhang, H. et al. Drug delivery systems for differential release in combination therapy. Expert opinion on drug delivery 2011, 8, (2), 171-190.
Zhang, J. et al. Biodegradable Electrospun Poly (Lactic Acid) Nanofibers for Effective Pm 2.5 Removal. Macromolecular Materials and Engineering 2019, 304 (10), 1900259.
Zhang, Q.; et al. Transboundary Health Impacts of Transported Global Air Pollution and International Trade. Nature 2017, 543 (7647), 705-709.
Zhang, R. et al. Nanofiber Air Filters with High-Temperature Stability for Efficient Pm2. 5 Removal from the Pollution Sources. Nano letters 2016, 16 (6), 3642-3649.
Zhang, S.; et al. Spider-Web-Inspired Pm0. 3 Filters Based on Self-Sustained Electrostatic Nanostructured Networks. Advanced Materials 2020, 32 (29), 2002361.
Zhang, Y. et al. Preparation of Nanofibrous Metal—Organic Framework Filters for Efficient Air Pollution Control. Journal of the American Chemical Society 2016, 138 (18), 5785-5788.
Zhao et al., Electrospun poly(L-lactic acid) nanofibers for nanogenerator and diagnostic sensor applications. Macromol. Mater. Eng. 302, 1600476 (2017).
Zheng et al., "Biodegradable triboelectric nongenerator as a lifetime designed implantable power source", 2016, Sci Adv 2:e1501478.
Zhu X, et al. Nanomedicine in the management of microbial infection—Overview and perspectives. Nano Today. 2014;9(4):478-498.
Zi et al., "Triboelectric-pyroelectric-piezoelectric hybrid cell for high-efficiency energy-harvesting and self-powered sensing", Adv Mater 27:2340-2347, 2015.
Baur D, Gladstone BP, Burkert F, Carrara E, Foschi F, Dobele S, Tacconelli E: Effect of antibiotic stewardship on the incidence of infection and colonisation with antibiotic-resistant bacteria and Clostridium difficile infection: a systematic review and meta-analysis. Lancet Infect Dis 2017, 17(9):990-1001.
BCC Research—Global Markets for Drug-Device Combinations, Jan. 2015. PHM045D.
Beaudet J, Tulman ER, Pflaum K, Liao X, Kutish GF, Szczepanek SM, Silbart LK, Geary SJ: Transcriptional Profiling of the Chicken Tracheal Response to Virulent Mycoplasma gallisepticum Strain Rlow. Infect Immun 2017, 85(10).
Blake KM, Carrigan SO, Issekutz AC, Stadnyk AW: Neutrophils migrate across intestinal epithelium using beta2 integrin (CD11b/CD18)-independent mechanisms. Clin Exp Immunol 2004, 136(2):262-268.
Creech et al., "Prevention of Recurrent Staphylococcal Skin Infections," Infect Dis Clin North Am. Sep. 2015; 29(3):429-464.
DeLeo FR, Diep BA, Otto M: Host defense and pathogenesis in *Staphylococcus aureus* infections. Infect Dis Clin North Am 2009, 23(1):17-34.
Garland MJ(1), Migalska K, Mahmood TM, Singh TR, Woolfson AD, Donnelly RF. Microneedle arrays as medical devices for enhanced transdermal drug delivery Expert Rev Med Devices. Jul. 2011;8(4):459-82.
Gordon CP, Williams P, Chan WC: Attenuating *Staphylococcus aureus* virulence gene regulation: a medicinal chemistry perspective. J Med Chem 2013, 56(4):1389-1404.
Haddadin et al., "Methicillin resistant *Staphylococcus aureus* (MRSA) in the intensive care unit," Postgraduate Medical Journal 2002; 78:385-392.
Hauert AB, Martinelli S, Marone C, Niggli V: Differentiated HL-60 cells are a valid model system for the analysis of human neutrophil migration and chemotaxis. Int J Biochem Cell Biol 2002, 34(7):838-854.
Infection Control Today, "New Research Estimates MRSA Infections Cost U.S. Hospitals $3.2 Billion to $4.2 Billion Annually,"<https://www.infectioncontroltoday.com/view/new-research-estimates-mrsa-infections-cost-us-hospitals-32-billion-42-billion-annually> dated May 16, 2005.
DeLeo et al., "Reemergence of antibiotic-resistant *Staphylococcus aureus* in the genomics era," JCL, 2009, 119, 2464-2474.
Jin Y, Li M, Shang Y, Liu L, Shen X, Lv Z, Hao Z, Duan J, Wu Y, Chen C et al: Sub-Inhibitory Concentrations of Mupirocin Strongly Inhibit Alpha-Toxin Production in High-Level Mupirocin-Resistant MRSA by Down-Regulating agr, saeRS, and sarA. Front Microbiol 2018, 9:993.
Kalali Y, Haghighat S, Mahdavi M: Passive immunotherapy with specific IgG fraction against autolysin: Analogous protectivity in the MRSA infection with antibiotic therapy Immunol Lett 2019, 212:125-131.
McHugh et al., Fabrication of fillable microparticles and other complex 3D microstructures. Science 2017, 357, (6356), 1138.
Klein et al., "National Costs Associated With Methicillin-Susceptible and Methicillin-Resistant *Staphylococcus aureus* Hospitalizations in the United States, 2010-2014," Clinical Infectious Diseases, vol. 68, Issue 1, Jan. 1, 2019, pp. 22-28.
Lausen M, Pedersen MS, Rahman NSK, Holm-Nielsen LT, Farah FYM, Christiansen G, Birkelund S: Opsonophagocytosis of Chlamydia pneumoniae by Human Monocytes and Neutrophils. Infect Immun 2020, 88(7).
Lokuta MA, Nuzzi PA, Huttenlocher A: Analysis of neutrophil polarization and chemotaxis. Methods Mol Biol 2007, 412:211-229.
Luzuriaga MA(1), Berry DR, Reagan JC, Smaldone RA, Gassensmith JJ. Biodegradable 3D printed polymer microneedles for transdermal drug delivery. Lab Chip. Apr. 17, 2018;18(8):1223-1230.
McAllister DV(1), Wang PM, Davis SP, Park JH, Canatella PJ, Allen MG, Prausnitz MR. Microfabricated needles for transdermal delivery of macromolecules and nanoparticles: fabrication methods and transport studies. Proc Natl Acad Sci USA. Nov. 25, 2003;100(24):13755-60.
Millius A, Weiner OD: Chemotaxis in neutrophil-like HL-60 cells. Methods Mol Biol 2009, 571:167-177.
Montgomery CP, Boyle-Vavra S, Daum RS: Importance of the global regulators Agr and SaeRS in the pathogenesis of CA-MRSA USA300 infection. PLoS One 2010, 5(12):e15177.
WHO, "New report calls for urgent action to avert antimicrobial resistance crisis," <https://www.who.int/news/item/29-04-2019-new-report-calls-for-urgent-action-to-avert-antimicrobial-resistance-crisis> dated Apr. 29, 2019.

(56) References Cited

OTHER PUBLICATIONS

Nielsen A, Mansson M, Bojer MS, Gram L, Larsen TO, Novick RP, Frees D, Frokiaer H, Ingmer H: Solonamide B inhibits quorum sensing and reduces *Staphylococcus aureus* mediated killing of human neutrophils. PLoS One 2014, 9(1):e84992.

O'Riordan K, Lee JC: *Staphylococcus aureus* capsular polysaccharides. Clin Microbiol Rev 2004, 17(1):218-234.

Parlet CP, Kavanaugh JS, Crosby HA, Raja HA, El-Elimat T, Todd DA, Pearce CJ, Cech NB, Oberlies NH, Horswill AR: Apicidin Attenuates MRSA Virulence through Quorum-Sensing Inhibition and Enhanced Host Defense. Cell Rep 2019, 27(1):187-198 e186.

Pressmeddelande, "Microneedle Drug Delivery Systems Market 2018 Segmentation, Demand, Growth, Trend, Opportunity and Forecast to 2023," My News Desk, <https://www.mynewsdesk.com/se/probe-way/pressreleases/microneedle-drug-delivery-systems-market-2018-segmentation-demand-growth-trend-opportunity-and-forecast-to-2023-2672909> dated Sep. 3, 2018.

Queck SY, Jameson-Lee M, Villaruz AE, Bach TH, Khan BA, Sturdevant DE, Ricklefs SM, Li M, Otto M: RNAIII-independent target gene control by the agr quorum-sensing system: insight into the evolution of virulence regulation in *Staphylococcus aureus*. Mol Cell 2008, 32(1):150-158.

Resistance WHO-TICGIoA: No time to wait: Securing the future from drug-resistant infections. In.; 2019.

Rigby KM, DeLeo FR: Neutrophils in innate host defense against *Staphylococcus aureus* infections. Semin Immunopathol 2012, 34(2):237-259.

Schutze GE, Hall MA, Baker CJ, Edwards MS: Role of neutrophil receptors in opsonophagocytosis of coagulase-negative staphylococci. Infect Immun 1991, 59(8):2573-2578.

Sutton et al., "Hospital-, Health Care-, and Community-Acquired MRSA: Estimates From California Hospitals, 2013," <https://www.hcup-us.ahrq.gov/reports/statbriefs/sb212-MRSA-Hospital-Stays-California-2013.jsp> dated Oct. 2016.

Thammavongsa V, Kim HK, Missiakas D, Schneewind O: Staphylococcal manipulation of host immune responses. Nat Rev Microbiol 2015, 13(9):529-543.

Tong SY, Davis JS, Eichenberger E, Holland TL, Fowler VG, Jr.: *Staphylococcus aureus* infections: epidemiology, pathophysiology, clinical manifestations, and management. Clin Microbiol Rev 2015, 28(3):603-661.

Varrone JJ, de Mesy Bentley KL, Bello-Irizarry SN, Nishitani K, Mack S, Hunter JG, Kates SL, Daiss JL, Schwarz EM: Passive immunization with anti-glucosaminidase monoclonal antibodies protects mice from implant-associated osteomyelitis by mediating opsonophagocytosis of *Staphylococcus aureus* megaclusters. J Orthop Res 2014, 32(10):1389-1396.

Varrone JJ, Li D, Daiss JL, Schwarz EM: Anti-Glucosaminidase Monoclonal Antibodies as a Passive Immunization for Methicillin-Resistant *Staphylococcus aureus* (MRSA) Orthopaedic Infections. Bonekey Osteovision 2011, 8:187-194.

Vysakh et al., "A Comparative Analysis of Community Acquired and Hospital Acquired Methicillin Resistant *Staphylococcus aureus*," J Clin Diagn Res. Jul. 2013; 7(7): 1339-1342.

Wang F, Gao W, Thamphiwatana S, Luk BT, Angsantikul P, Zhang Q, Hu CM, Fang RH, Copp JA, Pompattananangkul D et al: Hydrogel Retaining Toxin-Absorbing Nanosponges for Local Treatment of Methicillin-Resistant *Staphylococcus aureus* Infection. Adv Mater 2015, 27(22):3437-3443.

Zhou Y, Niu C, Ma B, Xue X, Li Z, Chen Z, Li F, Zhou S, Luo X, Hou Z: Inhibiting PSMalpha-induced neutrophil necroptosis protects mice with MRSA pneumonia by blocking the agr system. Cell Death Dis 2018, 9(3):362.

\* cited by examiner

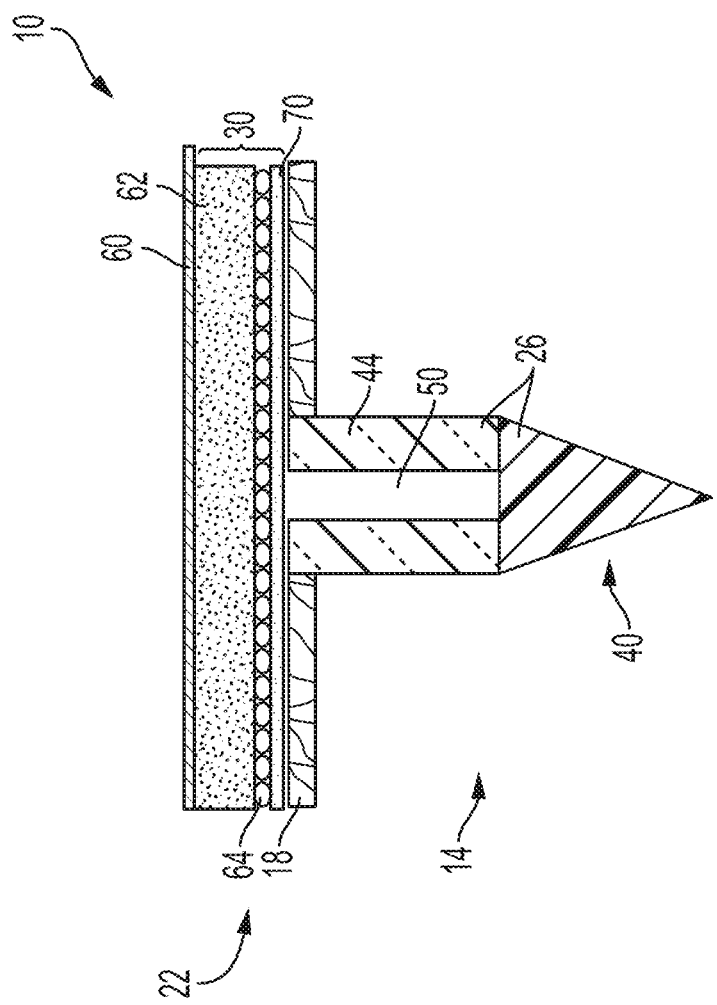
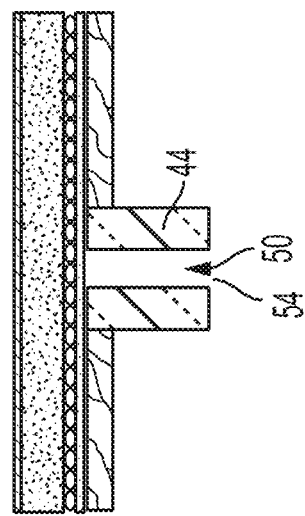
FIG. 1A
FIG. 1B

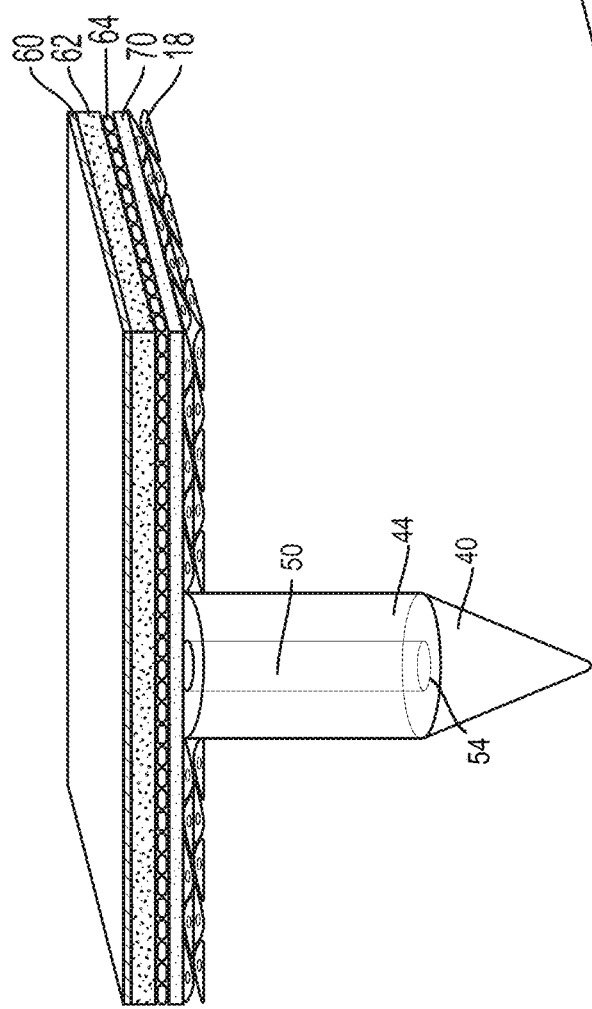
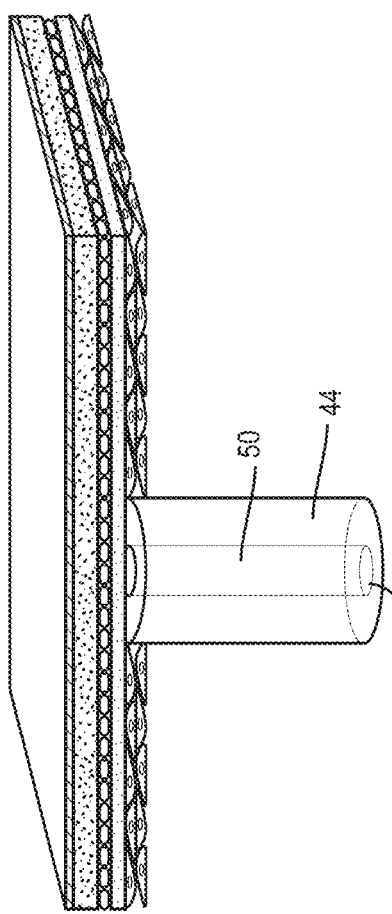

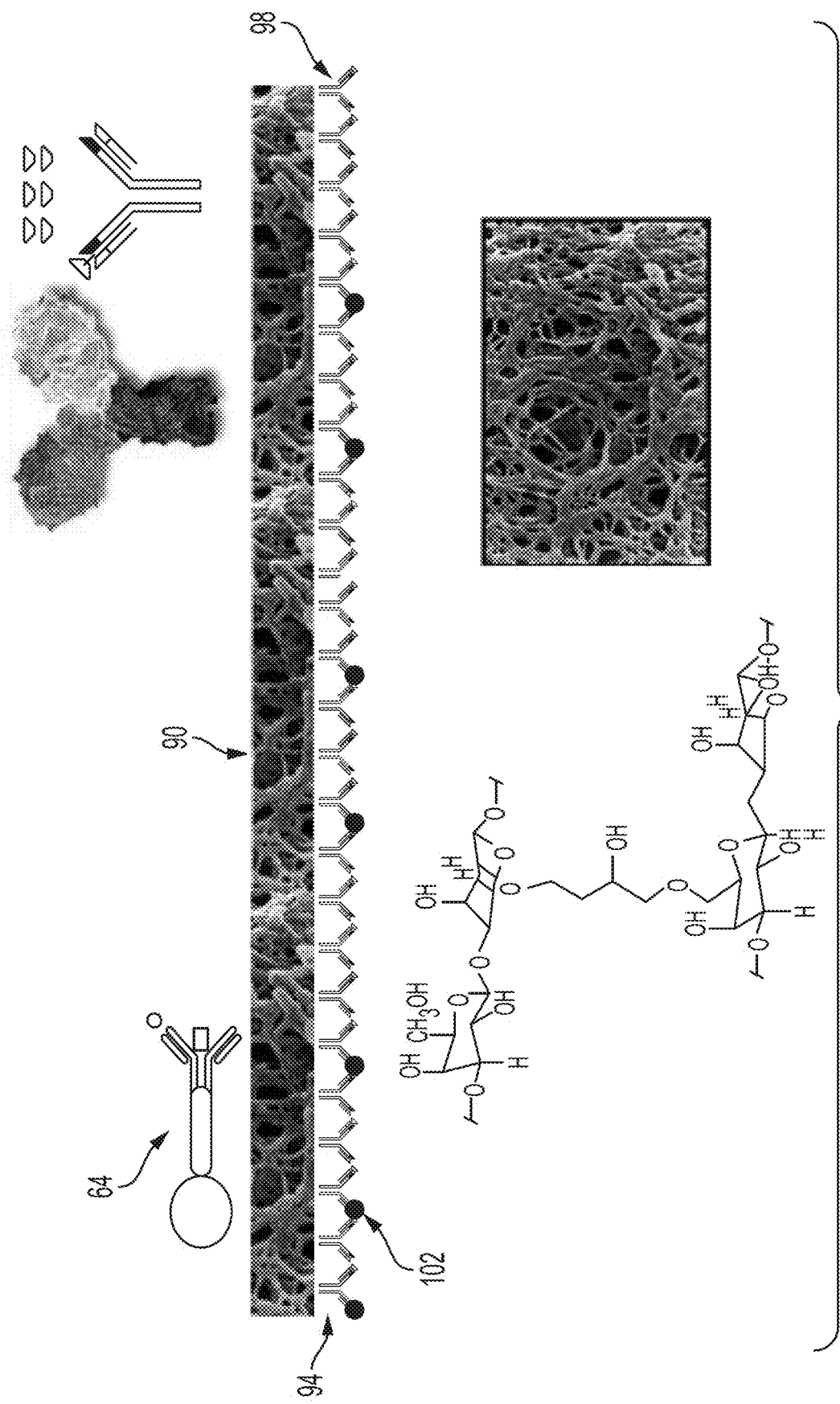

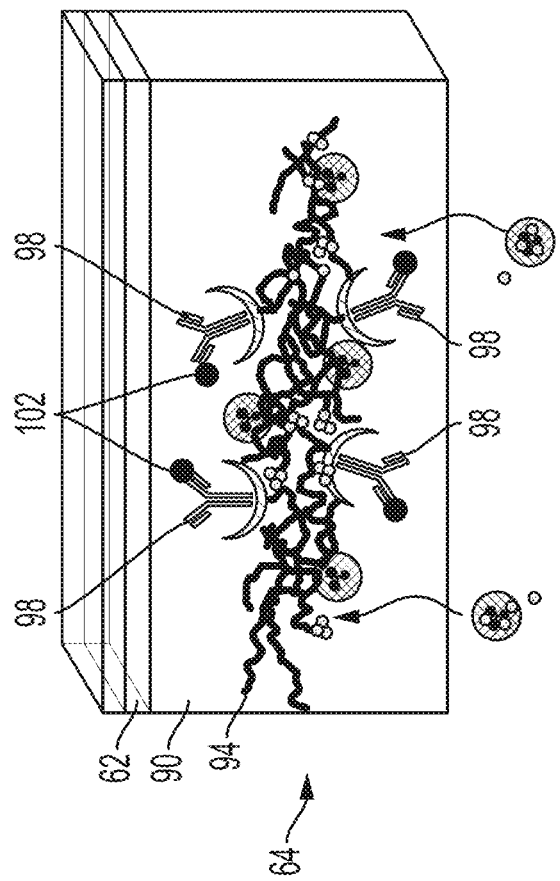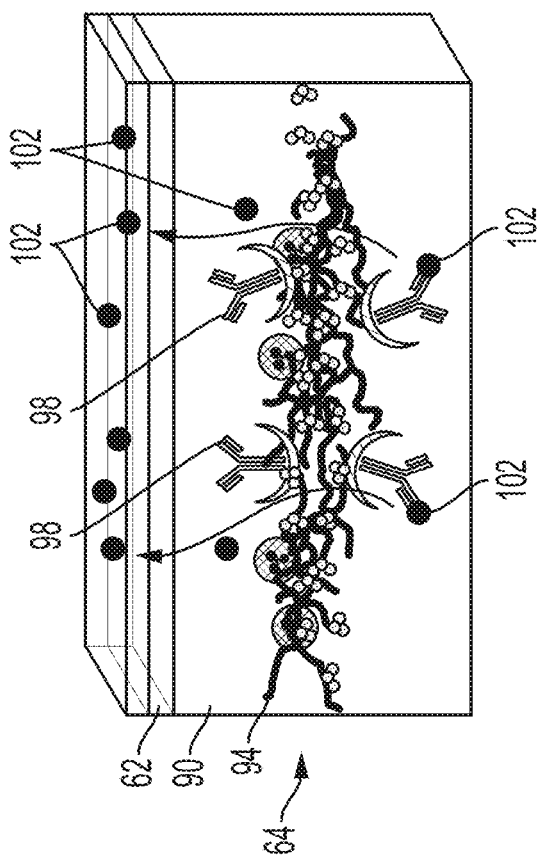

THERAPEUTIC BANDAGE

CROSS-REFERENCE TO RELATED APPLICATIONS

This application claims priority to U.S. Provisional Patent Application No. 62/987,494, filed Mar. 10, 2020, the entire contents of which is incorporated by reference herein.

BACKGROUND

Chronic non-healing skin wounds and skin and soft tissue infections (SSTIs) such as those caused by methicillin resistant *Staphylococcus aureus* (MRSA) and other bacteria are easily acquired in a variety of settings (e.g., daycare facilities, college dorm rooms, long-term care facilities, and hospitals or other healthcare establishments). SSTIs are typically treated topically, with or without high-dose antibiotic therapy. If improperly treated, these infections can penetrate deeper layers of skin, necessitating more aggressive surgical remedies to remove puss and necrotic tissue and to properly irrigate the wound. Moreover, the infection may enter blood vessels, allowing it to become established in distant tissues as well as potentially life-threatening sepsis. There are approximately 120,000 hospitalizations and 20,000 deaths per year attributable to MRSA infections, for example, but also 11.6 million ambulatory care visits per year for SSTIs, many of which are the result of chronic infections. Current treatments for these infections are costly and frequently ineffective. That is, currently available bandages do very little by way of immune modulation or the sequestration of toxins and microorganisms. Moreover, current topical treatment approaches for treating MRSA, and other SSTIs, are frequently ineffective for the following reasons: (i) poor drug delivery to dermal tissue due to the barrier function of the stratum corneum; (ii) the development of antibiotic-resistant bacterial strains including MRSA and VRSA (vancomycin-resistant *Staphylococcus aureus*), and (iii) a sub-optimal approach for manipulating the immunological microenvironment within the dermal tissue. Also, the current standard of care often includes minor surgery on the infection (incision and drainage) followed by high-dose oral antibiotic therapy. This approach is invasive and expensive and can result in off-target complications including disruption of the intestinal microbiome resulting in life threatening *C. difficile* infections. Further, the overuse of antibiotics is driving many microorganisms to develop antibiotic resistance, a phenomenon that the World Health Organization characterizes as 'one of the biggest threats to global health, food security, and development today. Finally, the known treatments are often not effective in achieving complete bacterial clearance, so infections often recur.

SUMMARY

In one embodiment, a therapeutic bandage is provided including a bandage matrix and a plurality of microneedles extending from the bandage matrix, each of the plurality of microneedles including a first layer that encapsulates a first immunomodulatory compound and a second layer that encapsulates a second immunomodulatory compound. The first layer is configured to release the first immunomodulatory agent at a first rate and the second layer is configured to release the second immunomodulatory agent at a second rate that is slower than the first rate. The first layer is positioned at a distal end of the second layer, and the second layer defining a channel extending from the distal end to the bandage matrix. The bandage matrix includes a hydration layer and a sequestration layer, the hydration layer is configured to absorb a foreign agent removed from a skin infection and the sequestration layer is configured to bind to the foreign agent removed. The bandage matrix includes a cellulose layer that is configured to bond to a biofilm resulting from the skin infection.

In another embodiments, a therapeutic bandage includes a bandage matrix and an array of microneedles extending from the bandage matrix. Each of the microneedles includes a first layer that encapsulates a first immunomodulatory compound and a second layer that encapsulates a second immunomodulatory compound. The array of microneedles is configured to guide foreign agents affected by the first immunomodulatory compound, the second immunomodulatory compound, or the first and second immunomodulatory compounds from one or more skin layers of a user to the bandage matrix such that the bandage matrix absorbs and captures the foreign agents.

In another embodiment, a therapeutic bandage includes a bandage matrix and at least one biodegradable microneedle extending from the bandage matrix. The at least one microneedle includes a base including a first end that is coupled to the bandage matrix, a second end opposite the first end, and a channel extending therethrough from the first end to the second end, and a tip coupled to the second end of the base. The tip is formed from a first material that encapsulates a first immunomodulatory compound and the base is formed from a second material that encapsulates a second immunomodulatory compound. The first material is configured to dissolve at a first rate and the second material is configured to dissolve at a second rate that is less than the first rate. The first immunomodulatory agent and the second immunomodulatory agent establish a chemotactic gradient within one or more skin layers. The channel is configured to guide foreign agents affected by the first immunomodulatory compound, the second immunomodulatory compound, or the first and second immunomodulatory compounds from the one or more skin layers of a user to the bandage matrix such that the bandage matrix absorbs and captures the foreign agents.

In another embodiment, a method of treating a skin infection or skin condition is provided including administering, via a first layer of a microneedle, a first immunomodulatory compound beneath the skin, administering, via a second layer of the microneedle, a second immunomodulatory compound beneath the skin, and draining phagocytic cells effected by the first immunomodulatory compound and the second immunomodulatory compound through a channel in the microneedle.

In another embodiment, a method of treating a skin infection or skin condition in humans and animals includes administering, via a first layer of a microneedle, a first immunomodulatory compound to a first layer of the skin or a biofilm layer, administering, via a second layer of the microneedle, a second immunomodulatory compound to a second layer of skin or the biofilm layer, and absorbing, by a bandage matrix, foreign agent affected by the first immunomodulatory compound, the second immunomodulatory compound, or the first and second immunomodulatory compounds. The second layer of the skin may be the same or different than the first layer of the skin.

Other aspects of the invention will become apparent by consideration of the detailed description and accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A illustrates a schematic view of a therapeutic bandage according to one embodiment.

FIG. 1B illustrates a schematic of a portion of the therapeutic bandage of FIG. 1A.

FIG. 1C illustrates another schematic view of the therapeutic bandage of FIG. 1A.

FIG. 1D illustrates a schematic of a portion of the therapeutic bandage of FIG. 1A.

FIG. 3A illustrates a portion of the therapeutic bandage of FIG. 1A.

FIG. 3B illustrates another view the portion of the therapeutic bandage of FIG. 3A.

FIG. 3C illustrates another view the portion of the therapeutic bandage of FIG. 3A.

DETAILED DESCRIPTION

Figure 2C:
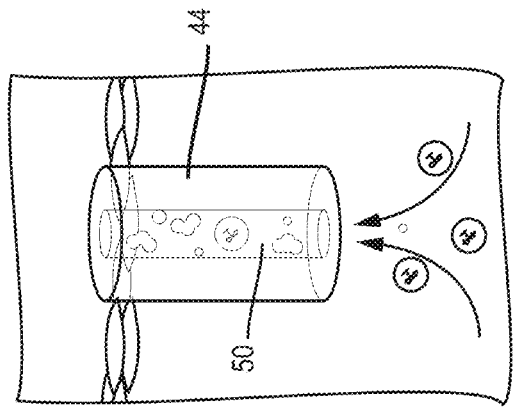
FIG. 2C illustrates the portion of the therapeutic bandage of FIG. 1A and interaction with underlying tissue.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

FIGS. 1A and 1B illustrate a therapeutic bandage 10 including a first or subcutaneous portion 14 that extends through outer layer (e.g., epidermis) of the skin 18 of a user and is positioned under the skin 18. The therapeutic bandage 10 also includes a second portion 22 that is positioned on or above the skin 18. The first portion 14 includes a plurality of dual-layer microneedles 26 (only one needle of the plurality of needles is shown in FIG. 1A), and the second portion 22 includes a bandage matrix 30. The plurality of dual-layer microneedles 26 are arranged in an array of microneedles 26 (e.g., an array with a density of about 1,200 microneedles per square inch of the bandage matrix 30). The plurality of microneedles 26 are at least temporarily coupled to the bandage matrix 30. The bandage matrix 30 is positionable or coupleable to a surface of the skin 18 such that the plurality of microneedles 26 penetrate the skin 18. That is, the microneedles 26 penetrate through the epidermis layer of the skin 18 (and the biofilm, if present) such that a portion becomes lodged in the dermis layer of the skin 18. The dermis layer is vascular.

With further reference to FIGS. 1A, 1B, 4A, and 4B, each of the plurality of microneedles 26 include a tip 40 (e.g., first needle layer) and a base 44 (e.g., second needle layer). The tip 40 is formed from a first polymeric material and encloses (e.g., suspends, encapsulates) a first immunomodulatory compound, a biological agent, an antimicrobial agent, or a combination of a immunomodulatory compound, a biological agent, and an antimicrobial agent. In the illustrated embodiment, the tip 40 is substantially conical, although the tip 40 may be other suitable shapes in other or alternative embodiments. The first polymeric material dissolves at a first rate. The first polymeric material may be, for example, a mixture of polyvinylpyrrolidone (PVP) and polyvinyl alcohol (PVA), although the first polymeric material may be any suitable material in other or alternative embodiments.

The base 44 includes a first (e.g., distal) end coupled to the tip 40, a second end coupled to the bandage matrix 30, and a channel 50 (e.g., microchannel or aperture) extending therethrough (also see FIG. 4A) between the first end and the second end. In the illustrated embodiment, the base 44 is substantially cylindrical, but in other or additional embodiments, the base 44 may be any suitable shape. The base 44 is formed from a second polymeric material. The second polymeric material may be, for example, poly(lactic-co-glycolic acid) (PLGA), although the second polymeric material may be any suitable material in other or alternative embodiments. The base 44 encloses (e.g., suspends, encapsulates) a second immunomodulatory compound. Like the tip 40, the base 44 may further enclose one or more biological agents, antimicrobial agents or both. The second polymeric material dissolves at a second rate that is slower than the first rate.

The microneedles 26 are non-toxic and biodegradable. In the illustrated embodiment, the tip 40 has a first length, and the base 44 has a second length that is equal to the first length. In the illustrated embodiment, the first length and the second length are 600 microns. In other or alternative embodiments, may have any suitable lengths. For example, in other embodiments, either or both of the first length or the second length may range from 100 microns to 600 microns. Moreover, in some embodiments, the total length of the microneedles 26 (e.g., the sum of the first length and the second length) may range from 200 microns to 1200 microns. Accordingly, and as discussed in greater detail below, the microneedles 26 are configured to deliver different biologically active compounds to different tissue depths thereby instigating a specific response for a specific type of pathogen or other foreign agent (for example, and without limitation, neoplasms, liver spots, poison ivy, poison oak, poison sumac, or tattoo ink). In some embodiments, the biologically active compounds may be instigate a specific response to other types of skin conditions, such as hereditary skin disorders (e.g., vitiligo), auto-immune disorders (e.g., lupus, scleroderma), and/or age-related degeneration of the skin (e.g., discoloration and/or wrinkling of skin). Additionally, in other or alternative embodiments, the microneedles 26 may include additional layers, which may be formed from a polymeric material and may enclose (e.g., suspend, encapsulate) additional immunomodulatory compounds, anti-microbial compounds, biologically active compounds, or a combination thereof. The sequential delivery of biologically active materials in close proximity to one another (via the co-localization of the tips 40 of the microneedles 26 and the base of the 44 of the microneedles 26) facilitates a two-phase movement or a three-phase movement of leukocytes into the tissue as described below by virtue of establishing chemokine gradients. This proximity augments egress of bacteria-laden leukocytes out of the tissue, via the microchannel 50 and into the bandage matrix.

In the illustrated embodiment, each of the plurality of microneedles 26 is configured to match or closely match the biological process of the infectious agent of a MRSA skin infection. In other or additional embodiments, the microneedles may be configured to match or closely match the biological processes of the infectious agents of other types of infections or other types of foreign agents. In the example of MRSA, MRSA evades host defenses in part by secreting many virulence factors, which disrupt neutrophil function. Neutrophils are recognized as the key host effector cell population for phagocytosing and killing MRSA. MRSA counteracts neutrophil function with an arsenal of its own, which includes neutrophil-killing toxins such as the Panton-Valentine leucocidin (PVL), alpha-toxin, phenol-soluble modulins, among others. In the initial stages of MRSA infection, the bacterium is only mildly pathogenic, growing in small planktonic microcolonies. Upon sensing a bacterial community, these microcolonies secrete quorum-sensing signals via a Agr two-component regulatory system and switch to a hyper-virulent form while initiating the formation of impenetrable biofilms. One goal of the therapeutic bandage 10 is to prevent this switch using a new class of 'virulence inhibiting' antibiotics, as discussed below. Neutrophils traffic into inflamed tissues following a chemotactic gradient in response to bacterial products (e.g., N-formylmethionyl-leucyl-phenylalanine (fMLF)), or chemokines (e.g., interleukin-8 (IL-8)) released by leukocytes and other cells, often in response to tissue damage.

Although only described in the context of a single microneedle 26, the following process applies to each of the microneedles 26 of the therapeutic bandage 10. As shown in FIG. 2A, after application of the bandage 10 to the site of interest, the polymeric material of the tip 40 begins to dissolve at the first rate, which is about 15 minutes to 30 minutes. As the tip 40 dissolves, the first immunomodulatory compound, the biological agent, and the antimicrobial agent encapsulated in the first polymeric material are released into the tissue beneath the skin 18. As the tip 40 dissolves, neutrophils migrate out of local capillary beds and into the tissue. In the illustrated embodiment, the first immunomodulatory compound is a chemokine (or combination of chemokines), which influences the migration of white blood cells (e.g., macrophages and neutrophils) from the blood stream into the infected area. In the illustrated embodiment, the first immunomodulatory compound is IL-8 having a concentration ranging from 1 nM to 10 nM and fMLF having a concentration of ranching 200 nM to 1,000 nM, which may induce robust neutrophil infiltration and priming/activation. In other embodiments, any of the known classes of chemokines or combinations of classes of chemokines may be used. Known, classes of chemokines include, but are not limited to, lipids (e.g., PGE2, platelet activating factor (PAF)), N-formylated peptides (e.g., bacterial, mitochondrial, or other FPR1, 2 and 3 agonists, such as fMLF, fMMYALF), eicosinoids (e.g., lipoxin A4) and other small molecules (e.g. pepducins, host-derived peptides, complement anaphylotoxins (C5a), or small proteins peptides), or proteins (e.g., CXCL8 and/or CXCL2), small molecules including leukotrienes (e.g., LTB4), cytokines (e.g., interleukin-8 (IL-8), IL-17A/IL-23), methylated BSA and/or any other suitable compound.

The biological agent helps the body fight the bacteria or infection agent (e.g., MRSA) and facilitate wound disinfection by "opsinizing" bacteria to enhance phagocytosis, and/or by attracting elements of the complement system. Opsinization is the process by which microorganisms are 'made tasty' to phagocytes upon coating of their outer surface with antibodies or complement components. Moreover, the biological agent can also neutralize bacterial toxins. The biological agent may include an organism-specific monoclonal antibody such as anti-Gmd (or other suitable MRSA-specific antibody), anti-MecA (PBP2a), anti-alpha toxin, and/or any suitable organism-specific monoclonal antibody (e.g., monoclonal antibody). In one example, monoclonal antibodies target a MRSA surface protein known as glucoseaminidase (gmd), which dramatically improves phagocytosis of planktonic MRSA as well as MRSA growing in megaclusters. This so-called 'opsonophagocytic activity' is initiated when the Fc portion of the monoclonal antibody is recognized by Fc-receptors (or CD14) expressed on the plasma membrane of neutrophils, triggering bacterial internalization.

The antimicrobial agents help disable the microorganism to facilitate their uptake by the naturally phagocytic cells. In the illustrated embodiment, the antimicrobial agents may include vancomycin, daptomycin, a combination of vancomycin and daptomycin, sitafloxicin, and/or any suitable antimicrobial agent or antibiotic (e.g., apicidin, savirin, ambuic acid, or any other member of this class of antibiotics, which may further include hydroxyketones, oxacillin, peptide-conjugated locked nucleic acids, tetrapeptide derivatives, ω-hydroxyemodin, or a combination thereof). Other or additional antimicrobial agents may be used instead of or in addition to other or additional embodiments. The cells effected by the first immunomodulatory compound, the biological compound, and the antimicrobial agent (e.g., phagocytic cells) begin to disinfect the tissue beneath the skin. It should be noted that the antibiotic dose is very low in comparison to current practice (administered orally or IV), and will remain localized to the skin (predominantly) thereby avoiding many of the consequences associated with high-dose antibiotic therapy, especially on the gut microbiome. The use of very low doses of locally administered antibiotics, and the use of 'virulence inhibitors' prevents the development of antibiotic resistance since these agents provide no growth/survival advantage to bacteria (unlike traditional bactericidal/bacteriostatic antibiotics). For example, the inhibition (via a virulence inhibitor antibiotic) of the Agr two-component quorum-sensing regulatory system prevents biofilm production and the expression of nearly 200 downstream virulence genes, many of which inhibit neutrophil function. Moreover, the inhibition of quorum sensing signals helps maintain MRSA in a planktonic state, making the bacterium much more susceptible to phagocytosis.

Figure 2A:
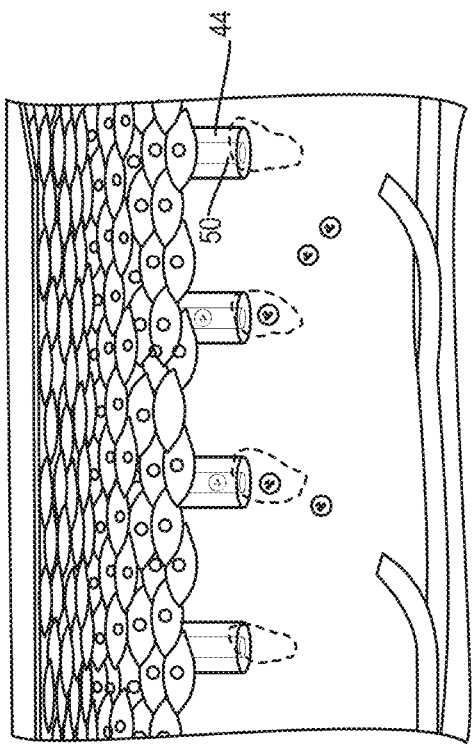
FIG. 2A illustrates a portion of the therapeutic bandage of FIG. 1A and interaction with underlying tissue.
Figure 2B:
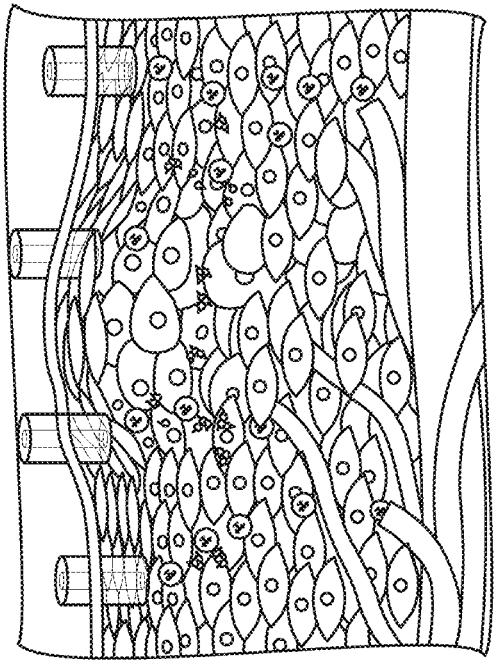
FIG. 2B illustrates the portion of the therapeutic bandage of FIG. 1A and interaction with underlying tissue.

With reference to FIGS. 1B, 1D, 2B, and 2C, once the tip 40 dissolves, the base 44 remains such that the channel 50 is accessible. Then the polymeric material of the base 44 begins to dissolve at the second rate, which is about 24 hours to about 72 hours. As the base 44 dissolves, the second immunomodulatory compound begins to release from the base 44, and cells effected by the contents of the tip 40 migrate towards the channel 50. More specifically, neutrophils (and/or other white blood cells, e.g., macrophages) released as the tip 40 dissolves acquire the pathogenic bacterial (e.g., infectious agent, foreign agent) within the wound and begin their migration towards the channel 50 due to the release of the second immunomodulatory compound. Because the channel 50 has the highest concentration of immunomodulatory compounds within and around an opening 54 (FIG. 1B) thereof, the phagocytic cells move toward and through the opening 54 (FIG. 2C). Accordingly, the phagocytic cells (with their recently-acquired bacterial, infectious agent or foreign agent payload) travel through the channel 50 due to capillary fluid movement, exit through the skin 18, and enter the bandage matrix 30 that is resting or adhered to the surface of the skin 18. In the illustrated embodiment, the second immunomodulatory compound is substantially similar to that of the first immunomodulatory compound. Accordingly, the second immunomodulatory compound is a combination of chemokines. Specifically, in the illustrated embodiment, the second immunomodulatory compound is IL-8 having a concentration ranging from 1 nM to 10 nM and fMLF having a concentration ranging from 200 nM to 1,000 nM. The second immunomodulatory compounds may be different than the first immunomodulatory compounds in other embodiments. Also, other or additional immunomodulatory compounds may be used instead of or in addition to the chemokines. Moreover, the biological agents, the antimicrobial agents or both discussed above may be used. If used, the biological agents, the antimicrobial agents, or both used in the base 44 may be the same or different than the biological agents, the antimicrobial agents, or both used in the tip 40.

With reference to FIGS. 1A, 1B, 2, and 3, the phagocytic cells (which often includes necrotic tissue, infectious agents, foreign agents, bacterial toxins, cellular debris and autolysis fluids) that move through the channel 50 of the base 40 of the microneedle 26 are absorbed and captured by the bandage matrix 30, which will be discussed in greater detail below.

The bandage matrix 30 includes a transparent film layer 60 (e.g., a barrier film layer formed from a polyurethane membrane), a first bandage layer 62 (e.g., hydration layer), a second bandage layer 64 (e.g., sequestration layer), and a wound contact (e.g., cellulose) layer 70. The layers may be coupled by adhesive (e.g., acrylic adhesive) or other suitable methods.

The hydration layer 62 defines a hydrodynamic gradient based on fluid capillary action using adsorbent hydrogel materials (e.g., calcium alginate) to hasten fluid efflux from the wound into the bandage matrix 30. In some embodiments, a third immunomodulatory compound may be included in the hydration layer to further attract phagocytic cells into deeper layers of the bandage matrix 30. In some embodiments, the hydration layer 62 may be formed from hydrogel impregnated with the third immunomodulatory compound (e.g., chemokine-impregnated), which is discussed in detail below. In the illustrated embodiment, the third immunomodulatory compound is substantially similar to that of the first and second immunomodulatory compounds. Accordingly, in the illustrated embodiment, the third immunomodulatory compound is IL-8 having a concentration ranging from 1 nM to 10 nM and fMLF having a concentration ranging from 200 nM to 1,000 nM. The third immunomodulatory compound may be different than the first and second immunomodulatory compounds in other embodiments. Moreover, biological agents, antimicrobial agents, or both discussed above may be also included in the hydration layer used. If used, the biological agents, the antimicrobial agents, or both used in the hydration layer 62 may be the same or different than the biological agents, the antimicrobial agents, or both used in the tip 40 and the base 44.

The sequestration layer 64, which is shown in FIGS. 3A-3B, may be positioned adjacent to the hydration layer 62. In the illustrated embodiment, the sequestration layer 64 includes a base layer 90 that is coupled to or coated with a capture layer 94 having one or more immobilized antibodies 98. Also, a ligand or dye 102 is bound to the one or more of the antibodies 98 as part of a detection/saturation reporter system. In the illustrated embodiment, the base layer 90 is 6% cross-linked agarose bound to protein A/G and the capture layer 94 includes monoclonal antibodies configured to attract or otherwise tightly adhere to the respective infectious agents or foreign agents (e.g., MRSA in this embodiment). The sequestration layer 64 sequesters the infectious agents or foreign agents and associated toxins. The dye 102 bound to the antibodies is released when the infectious agent or foreign agent is present. The dye 102 that is released diffuses radially into the hydration layer 62 becoming visible through the transparent film, thereby alerting the patient or healthcare worker that the therapeutic bandage 10 has reached its capacity and should be replaced.

In one specific embodiment, as wound exudate migrates into the therapeutic bandage 10, it will pass through the cellulose layer 70 (discussed below) and will encounter the base layer (e.g., the diffuse matrix of 6% beaded agarose covalently modified with Protein A or G), which binds to antibody Fc regions with high avidity. In this embodiment, the antibodies are monoclonal antibodies to Gmd, which will bind to and sequester any free bacteria which enter the bandage matrix 30. During manufacture, approximately 10% of the antibody binding sites will be occupied with recombinant Gmd-conjugated to 400 nm blue latex beads 102. As the capacity of the bandage 10 for MRSA binding is approached, the blue latex beads 102 will gradually be released, allowing them to diffuse into the hydrogel 62 where they will become visible to the naked eye through the clear, medical grade polyurethane barrier film. As noted above, this modified lateral flow immunoassay will report bandage saturation to the health care professional, triggering bandage removal and replacement.

The cellulose layer 70 provides a mechanism for microdebridement as the carbohydrate layer created by the cellulose intermingle with a carbohydrate layer of the infectious agent (e.g., the exopolysaccharide of the MRSA present in the biofilm at the surface of the wound) or foreign agent. That is, a biofilm developed by the wound (which often impedes proper wound healing) may grow into the cellulose layer, creating permanent points of attachment. Once the therapeutic bandage 10 is removed, the biofilm will remain associated (integral) with the cellulose layer 70, providing a mechanism for pain-free removal, obviating the need for surgical debridement. In addition, the cellulose layer 70 can serve as a reservoir for additional chemokines and antimicrobial agents should lab tests indicate such a need.

Many superficial skin wounds become chronically infected, which leads to the breakdown of the epidermis due to constant contact with bacterial enzymes and host derived toxic factors (e.g. reactive oxygen/nitrogen, proteolytic enzymes etc.). This can lead to the formation of 'chronic, non-healing wounds' requiring frequent surgical debridement procedures which are painful and expensive. The bacteria which colonize these wounds, including MRSA, in response to sensing quorum factor signals exit planktonic growth patterns and form biofilms which are nearly impregnable by small molecules due to the production of an exopolysaccharide protective outer shell. Accordingly, in some embodiments, the cellulose layer 70 be made of a cellulose $((C6H10O5)_x)$ (25 micron pore size) into which the exopolysaccharide will attach and intertwine with the cellulose matrix. Upon removal, the biofilm will remain attached to the cellulose layer 70, providing a mechanism for micro-debridement without surgical intervention. In other embodiment, a second approach to prevent biofilm production may be in the impregnation of the hydration layer (which may include 12.5% calcium alginate hydrogel) with anti-virulence therapeutic agents such as apicidin or other suitable antimicrobial agent or antibiotic (discussed above), which, by virtue of inhibiting the agr system will also prevent the transition into biofilm production. Alginate, for example, is a naturally occurring anionic and hydrophilic polysaccharide comprised of crosslinked (1-4)-linked β-d-mannuronic acid (M) and α-1-guluronic acid (G) monomers. Impregnation of calcium alginate with apicidin and the third immunomodulatory compound may be accomplished using supercritical $CO_2$, among other processes. Once the hydrogel becomes water-saturated (approximately 30-fold swelling), directional movement of water will cease, and fluid flow within the bandage 10 will become static. Thus, the remaining activity will be based on chemotaxis and drug diffusion. The impregnation of the third immunomodulatory compound may allow bacteria-laden (e.g., infectious agent-laden, foreign agent-laden, MRSA-laden) neutrophils to move several millimeters into the bandage matrix, providing a unique approach for disinfecting the wound. Taken together, these innovations may also speed healing by virtue of preventing 'collateral damage' from virulence factors normally released by the bacterium, and by preventing the formation of a surface biofilm.

As multiple applications of the therapeutic bandage may be needed, the penetration points of the microneedles will differ, allowing punctate healing over the entire wound bed. Thus, different portions of the wound may be at different stages in the disinfection/wound-healing process. Over time (and with repeated applications), the wound will be sufficiently disinfected to allow normal wound healing to proceed in an unhindered fashion.

Figures 4A, 4B:
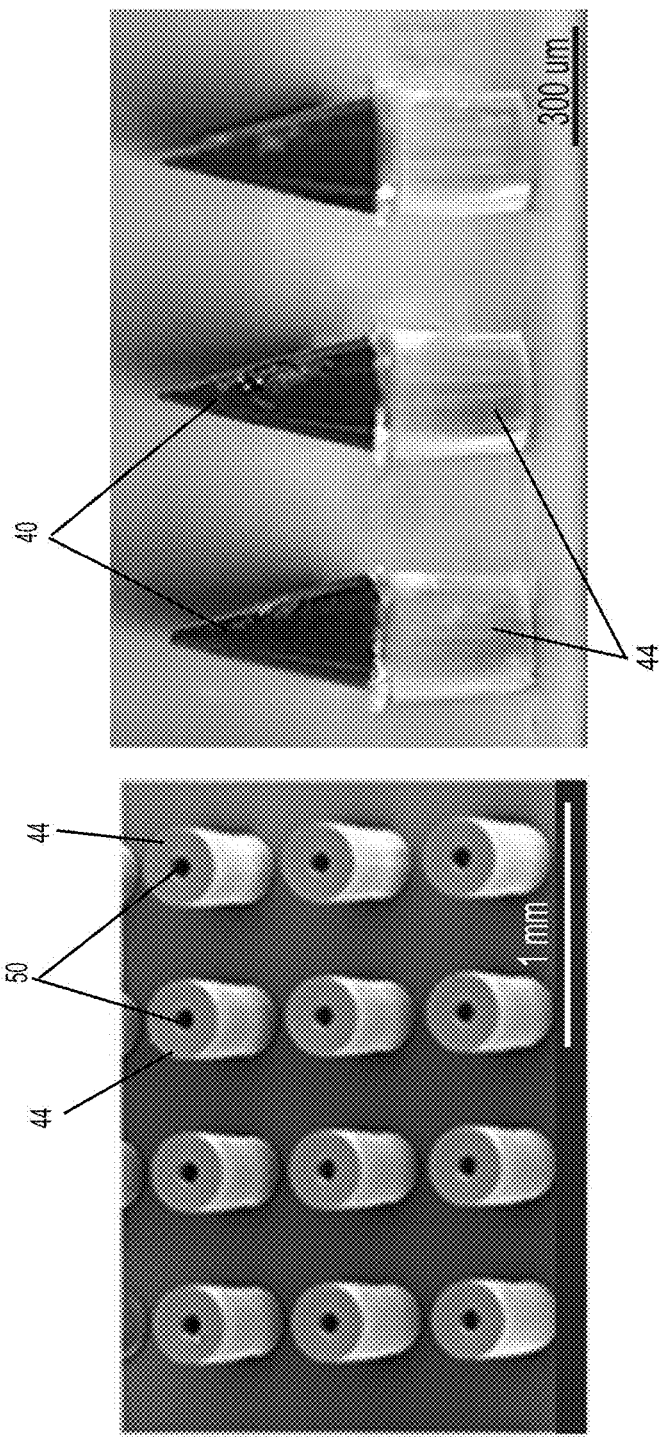
FIG. 4A illustrates a first portion of the therapeutic bandage of FIG. 1A.
FIG. 4B illustrates the first portion of FIG. 4A coupled to a second portion of the therapeutic bandage of FIG. 1A.
Figure 4D:
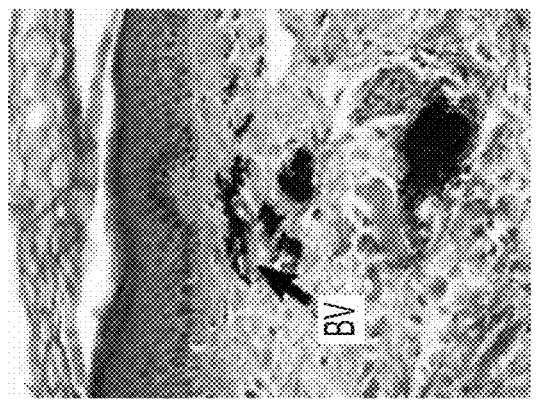
FIG. 4D illustrates a longitudinal section of explanted human skin showing spacing of microneedle deposition in the dermal layer following the therapeutic bandage application.
Figure 4E:
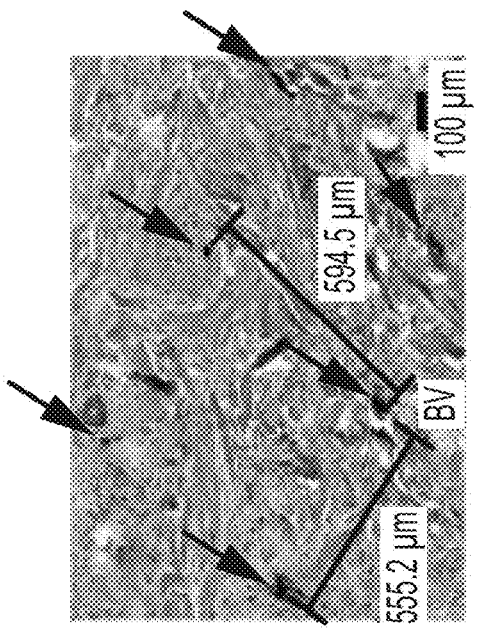
FIG. 4E illustrates explanted human skin showing contents released by following the therapeutic bandage application.
Figure 4C:
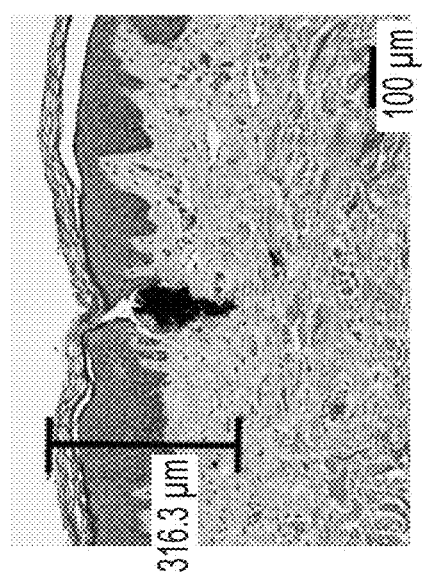
FIG. 4C illustrates a transverse section of explanted human skin following a therapeutic bandage application.
Figure 5:
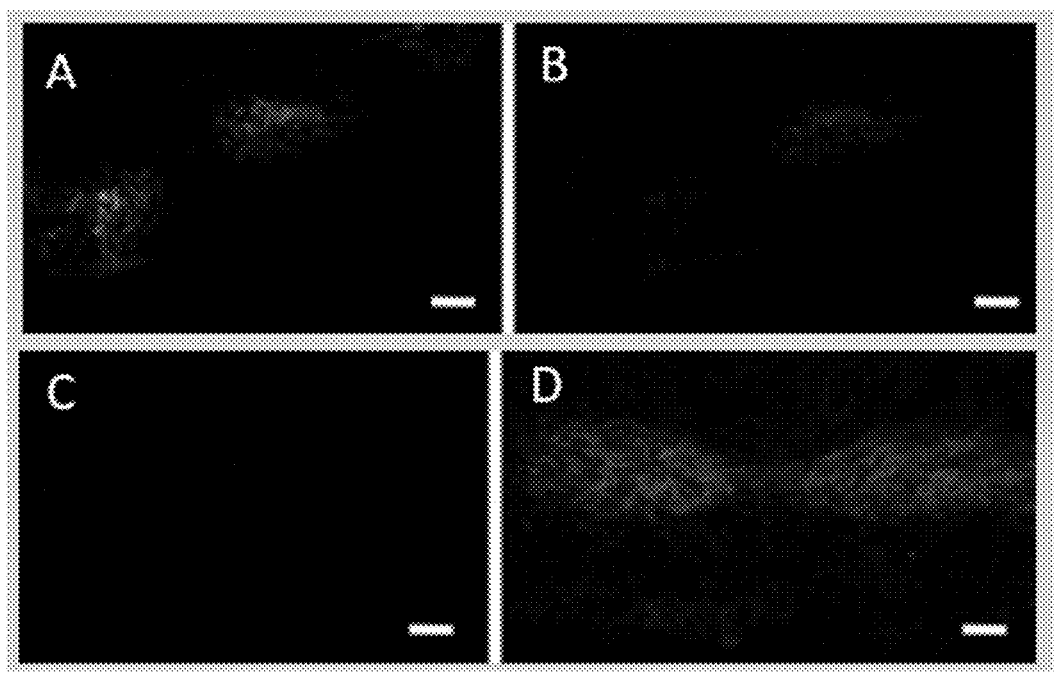
FIG. 5 illustrates the epifluorescence microscopy results after contents from the therapeutic bandage are released into the skin layers of explanted skin.

FIG. 4A illustrates a microneedle base 44 showing the hollow channel 50. FIG. 4B illustrates the microneedle base 44 coupled to the rapid-dissolving tips 40, which include tattoo ink. In one embodiment, the therapeutic bandage 10 may be producing the microneedles 26 and then coupling the microneedles 26 to the bandage matrix 30. In some embodiments, the microneedles 26 may be integrally formed with a portion of the bandage matrix 30. The microneedles are produced by forming the base 44, with the microchannel 50, and loading the base 22 with the second immunomodulatory compound. The tip 40 is then produced and loaded with the first immunomodulatory compound. The tip 40 is then coupled to the base 44 to seal the microchannel 26. To test the mechanical strength of the microneedles 26, the tips 40 were loaded with insoluble tattoo ink (FIG. 4B). The microneedles 26 were then applied to cultured human skin explants using a 1 Newton application force. The tips 40 were sufficiently rigid to penetrate the epidermis (FIG. 4C) and deliver the tattoo ink in close proximity to dermal blood vessels ('Bv' in FIG. 4D). That is, FIG. 4C shows a transverse section of explanted human skin following bandage application, indicating the depth of penetration and payload deposition of insoluble tattoo ink into the dermal layer. More specifically, FIG. 4C shows the depth of tissue penetration and deposition of the ink after an insertion force of 1N. FIG. 4D shows the ink in the dermal layer adjacent to blood vessels in explained human skin. FIG. 4E illustrates a longitudinal section of explanted human skin showing spacing of microneedle deposition in the dermal layer. The kinetics of drug release were then measured using epifluorescence microscopy and two fluorescent dyes. BODIPY-vancomycin (green) was loaded in the tips 40, while sulforhodamine B was loaded into the base 44. As anticipated, the tips 40 dissolved within 30 minutes and delivered the BODIPY-vancomycin into the dermal layer of skin, with a diffusion radius of approximately 440 microns to 600 microns (FIG. 5 at A). By one hour after bandage application, the burst release of DODIPY-vancomycin (green) from the tip 40 had diffused and was no longer detectable. Conversely, the red fluorescence was released much more slowly (after about one hour) from the microneedle base 44, with approximately equal diffusion radius (FIG. 5 at D). Moreover, as shown at FIG. 5 at B, the sulforhodamine B dye was barely visible after only 30 minutes.

The therapeutic bandage 10 discussed herein is suitable for use in healthcare settings including hospitals, outpatient clinics and nursing homes, as well as for over-the-counter applications and prescription-based applications for skin infections and conditions. Also in addition to being appropriate for any bacterial, fungal or viral skin infection, the therapeutic bandage 10 discussed herein may be suitable for the foreign agents of other skin conditions, such as poison ivy/oak/sumac, minor burns, tattoo removal, bio-threat agents, acne, contact sensitivities and allergic conditions including eczema, insect stings/bites, diabetic foot ulcers, pressure ulcers, venous ulcers, etc. Additionally, as noted above, the therapeutic bandage 10 discussed herein may be suitable other types of skin conditions, such as hereditary skin disorders (e.g., vitiligo), auto-immune disorders (e.g., lupus, scleroderma), and/or age-related degeneration of the skin (e.g., discoloration and/or wrinkling of skin). Pets and other companion animals (e.g. horses and some farm animals) also suffer from dermatological skin conditions including allergic eczema, MRSA infections and others. One embodiment of the current invention could be used to treat such animals by formulating the device with species-specific therapeutic agents in keeping with accepted veterinary practices.

The therapeutic bandage 10 discussed herein provides a highly targeted local therapy and promotes more rapid healing. It relies on the precise administration of immunomodulatory compounds to orchestrate the movement of leukocytes and other cell populations known or suspected to be associated with wound disinfection and healing, both temporally and spatially. That is, the therapeutic bandage 10 i) recruits high numbers of neutrophils (and/or other types of white blood cells, e.g., macrophages), the key type of white blood cell needed to clear the infection, into the infected tissue; (ii) manipulates the immunological environment within the dermal tissue to prevent neutrophil (and/or other types of white blood cell, e.g., macrophage) killing and maximize their ability to engulf and destroy the bacteria; and (iii) provides a mechanism for interstitial fluid movement, which facilitates the removal of pus, detritus, neutrophils (and/or other types of white blood cells, e.g., macrophages), bacterial toxins and bacteria to exit the wound and become entrapped in the bandage matrix 30. The plurality of microneedles 26 (i) deliver therapeutic agents (e.g., the first and second immunomodulatory compounds) into the dermal layer of infected skin to promote neutrophil (and/or other types of white blood cell, e.g., macrophage) movement into the wound plus additional agents to ensure their survival and maximizing their function; (ii) have a bi-directional channel allowing fluid communication between the bandage matrix 30 and the infected tissues to facilitate the egress from the wound, and (iii) a four-layer bandage matrix which entraps (e.g., absorbs and captures) wound exudate paired with a reporter system to alert healthcare workers when the bandage becomes saturated. The elements referenced above provide a 'three-phased chemokine' approach, which establishes a temporal and spatial gradient of chemo-attractants. The first wave of immunomodulatory compounds from the tip 40 of the microneedle 26 facilitates the movement of neutrophils (and/or other types of white blood cells, e.g., macrophages) first from blood into the wound, followed hours later by the second wave of immunomodulatory compounds emanating from the base 44 of the microneedle 26. The co-localization of the tips 40 of the microneedles 26 and the channel 50 is key to proper functioning helps funnel bacteria-laden (e.g., infectious agent-laden, foreign agent-laden) neutrophils (and/or other types of white blood cells, e.g., macrophages) toward the channel 50, where interstitial fluid movement will sweep them out of wound and into the bandage matrix 30. Once net fluid movement slows to a stop, the third wave of immunomodulatory compounds emanating from the water saturated hydration layer 62 will attract neutrophils (and/or other types of white blood cells, e.g., macrophages) into deeper layers of the bandage matrix 30. The immunomodulatory compounds, the biological agents, and the antimicrobial agents maximize neutrophil infiltration, prevent their inactivation, and hasten their movement out of the wound following uptake of infectious agents (or other foreign agents) thereby facilitating rapid wound disinfection and healing and preventing the spread of infectious organisms to visceral organs and to other individuals.

Moreover, the therapeutic bandage 10 discussed herein is minimally invasive and prevents dissemination of infectious organisms to visceral tissues, thereby mitigating a potentially life-threatening condition. For example, the microneedles 26 are small enough to avoid touching nerve endings, significantly reducing pain while penetrating the stratum corneum to enable effective drug delivery into the highly vascularized dermal layer of skin. In some instances, the therapeutic bandage can be self-administered by a patient, offering a high degree of patient compliance at a significantly reduced cost.

Various features and advantages of the invention are set forth in the following claims.

What is claimed is:

1. A therapeutic bandage comprising:

a bandage matrix; and an array of microneedles extending from the bandage matrix, each of the microneedles including a first layer that encapsulates a first immunomodulatory compound and a second layer that encapsulates a second immunomodulatory compound, wherein the array of microneedles is configured to guide foreign agents affected by the first immunomodulatory compound, the second immunomodulatory compound, or the first and second immunomodulatory compounds from one or more skin layers of a user to the bandage matrix such that the bandage matrix absorbs and captures the foreign agents.

2. The therapeutic bandage of claim 1, wherein the first layer is configured to release the first immunomodulatory agent at a first rate, and the second layer is configured to release the second immunomodulatory agent at a second rate that is less than the first rate, and wherein the first immunomodulatory agent and the second immunomodulatory agent establish a chemotactic gradient within the one or more skin layers.

3. The therapeutic bandage of claim 2, wherein the first layer defines a first length and the second layer defines a second length, the first layer being configured to release the first immunomodulatory agent at a first tissue depth, the second layer being configured to release the second immunomodulatory agent at a second tissue depth that is different than the first tissue depth.

4. The therapeutic bandage of claim 2, wherein the first layer is formed from a mixture of polyvinylpyrrolidone (PVP) and polyvinyl alcohol (PVA) and the second layer is formed from poly(lactic-co-glycolic acid) (PLGA).

5. The therapeutic bandage of claim 1, wherein the second layer includes a first end that is coupled to the bandage matrix and a second end opposite the first end, the first layer being positioned at the second end of the second layer.

6. The therapeutic bandage of claim 1, wherein the second layer includes a first end that is coupled to the bandage matrix, a second end opposite the first end, and a channel extending therethrough from the first end to the second end, the channel configured to guide the foreign agents to the bandage matrix.

7. The therapeutic bandage of claim 1, wherein the bandage matrix includes a hydration layer and a sequestration layer, the hydration layer is configured to absorb the foreign agents removed from a skin infection or skin condition and the sequestration layer is configured to bind to the foreign agents.

8. The therapeutic bandage of claim 7, wherein the bandage matrix includes a cellulose layer that is configured to bond to a biofilm resulting from the skin infection or skin condition.

9. The therapeutic bandage of claim 7, wherein the sequestration layer includes an antibody and a dye that is bound to the antibody, the antibody configured to bind at least one of the foreign agents and the dye configured to release from the antibody when the antibody binds the at least one foreign agent, the dye being visible from outside the bandage matrix when released.

10. A therapeutic bandage comprising:

a bandage matrix; and at least one biodegradable microneedle extending from the bandage matrix, the at least one microneedle including a base including a first end that is coupled to the bandage matrix, a second end opposite the first end, and a channel extending therethrough from the first end to the second end, and a tip coupled to the second end of the base, wherein the tip is formed from a first material that encapsulates a first immunomodulatory compound and the base is formed from a second material that encapsulates a second immunomodulatory compound, wherein the first material is configured to dissolve at a first rate and the second material is configured to dissolve at a second rate that is less than the first rate, wherein the first immunomodulatory agent and the second immunomodulatory agent establish a chemotactic gradient within one or more skin layers, and wherein the channel is configured to guide foreign agents affected by the first immunomodulatory compound, the second immunomodulatory compound, or the first and second immunomodulatory compounds from the one or more skin layers of a user to the bandage matrix such that the bandage matrix absorbs and captures foreign agents.

11. The therapeutic bandage of claim 10, wherein the first material is formed from a mixture of polyvinylpyrrolidone (PVP) and polyvinyl alcohol (PVA) and the second material is formed from poly(lactic-co-glycolic acid) (PLGA).

12. The therapeutic bandage of claim 10, wherein the base defines a first length and the tip defines a second length, the tip being configured to release the first immunomodulatory compound a first tissue depth, the base being configured to release the second immunomodulatory agent at a second tissue depth that is different than the first tissue depth.

13. The therapeutic bandage of claim 10, wherein the first material encapsulates a biological agent, an antimicrobial agent, or both.

14. The therapeutic bandage of claim 10, wherein the bandage matrix includes an antibody and a dye that is bound to the antibody, the antibody configured to bind at least one of the foreign agents and the dye configured to release from the antibody when the antibody binds the at least one foreign agent, the dye being visible from outside the bandage matrix when released.

15. The therapeutic bandage of claim 14, wherein the bandage matrix includes a cellulose layer that is configured to bond a biofilm resulting from a skin infection or skin condition.

16. A method of treating a skin infection or skin condition in humans and animals, the method comprising:
administering, via a first layer of a microneedle, a first immunomodulatory compound to a first layer of the skin or a biofilm layer;
administering, via a second layer of the microneedle, a second immunomodulatory compound to a second layer of the skin or the biofilm layer, the second layer of the skin may be the same or different than the first layer of the skin; and
absorbing, by a bandage matrix, foreign agents affected by the first immunomodulatory compound, the second immunomodulatory compound, or the first and second immunomodulatory compounds.

17. The method of claim 16, wherein administering, via the first layer of a microneedle, the first immunomodulatory compound to the first layer of the skin or the biofilm layer includes releasing the first immunomodulatory compound at a first rate, and wherein administering, via the second layer of the microneedle, the second immunomodulatory compound to the second layer of the skin or the biofilm layer includes releasing the second immunomodulatory compound at a second rate that is less than the first rate.

18. The method of claim 17, wherein releasing the first immunomodulatory compound at the first rate includes releasing the first immunomodulatory compound at a first tissue depth, and wherein releasing the second immunomodulatory compound at the second rate includes releasing the second immunomodulatory compound at a second tissue depth that is different than the first depth.

19. The method of claim 16, wherein absorbing, by the bandage matrix, the foreign agents includes binding at least one of the foreign agent to an antibody contained in the bandage matrix.

20. The method of claim 19, further comprising releasing a dye in the bandage matrix when the at least one foreign agent binds to the antibody, the dye being visible from an outside of the bandage matrix.

* * * * *